US008461310B2

(12) United States Patent
Uede et al.

(10) Patent No.: US 8,461,310 B2
(45) Date of Patent: Jun. 11, 2013

(54) ANTI-ADAM-15 ANTIBODIES AND UTILIZATION OF THE SAME

(75) Inventors: Toshimitsu Uede, Hokkaido (JP); Yutaka Matsui, Hokkaido (JP)

(73) Assignees: Gene Techno Science Co., Ltd., Hokkaido (JP); National University Corporation Hokkaido University, Hokkaido (JP)

(*) Notice: Subject to any disclaimer, the term of this patent is extended or adjusted under 35 U.S.C. 154(b) by 195 days.

(21) Appl. No.: 12/867,449

(22) PCT Filed: Feb. 12, 2009

(86) PCT No.: PCT/JP2009/052290
§ 371 (c)(1),
(2), (4) Date: Aug. 12, 2010

(87) PCT Pub. No.: WO2009/101968
PCT Pub. Date: Aug. 20, 2009

(65) Prior Publication Data
US 2010/0317835 A1    Dec. 16, 2010

(30) Foreign Application Priority Data

Feb. 14, 2008  (JP) ................. 2008-033354

(51) Int. Cl.
*C07K 16/00*    (2006.01)
(52) U.S. Cl.
USPC .................... 530/388.1; 530/388.8
(58) Field of Classification Search
None
See application file for complete search history.

(56) References Cited

U.S. PATENT DOCUMENTS

| 5,830,742 A | 11/1998 | Black et al. |
| 6,013,466 A | 1/2000 | Black et al. |

FOREIGN PATENT DOCUMENTS

| JP | 2003-523768 | 8/2003 |
| WO | WO 01/62905 | 8/2001 |

OTHER PUBLICATIONS

Skolnick and Fetrow. From genes to protein structure and function: novel applications of computational approaches in the genomic era. Trends in Biotechnology, 2000. vol. 18, pp. 34-39.*
Mac Callum, Martin, and Thornton. Antibody antigen interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*
Holm, Jafari, and Sundstrom. Functional mapping and single chain construction of the anti-cytokeratin 8 monoclonal antibody TS1. Molecular Immunology, 2007. vol. 44, pp. 1075-1084.*
Chen, Wiesmann, Fuh, Li, Christinger, McKay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*
Wu, Nie, Huse, and Watkins. Humanization of a murine monoclonal antibody by simultaneous optimization of frameowrk and CDR residues. Journal of Molecular Biology, 1999. vol. 294, pp. 151-162.*
Rudikoff, Giusti, Cook, and Scharff. Single amino acid substitution altering antigen binding specificity. Proceedings of the National Academy of Sciences, 1982. vol. 79 p. 1979.*
Alfandari et al. (1997) ADAM 13: A novel ADAM expressed in somitic mesoderm and neural crest cells during Xenopus laevis development, Dev. Biol. 182:314-330.
Almelda et al. (1995) Mouse egg integrin alpha-6-beta-1 functions as a sperm receptor, Cell 81:1095-1104.
Charrier et al. (2007) ADAM-15/Metargidin mediates homotypic aggregation of human T lymphocytes and heterotypic interactions of T lymphocytes with intestinal epithelial cells, J. Biol. Chem. 282:16948-16958.
Ham et al. (2002) ADAM15 is an adherens junction molecule whose surface expression can be driven by VE-cadherin, Exp. Cell Res. 279:239-247.
Herren et al. (2001) ADAM15 overexpression in NIH3T3 cells enhances cell-cell interactions, Exp. Cell Res. 271:152-160.
Horiuchi et al. (2003) Potential role for ADAM15 in pathological neovascularization in mice, Mol. Cell. Biol. 23:5614-5624.
Komiya et al. (2005) Expression of ADAM15 in rheumatoid synovium: up-regulation by vascular endothelial growth factor and possible implications for angiogensis, Arthritis Res. Ther. 7:R1158-R1173.

(Continued)

*Primary Examiner* — Mark Halvorson
(74) *Attorney, Agent, or Firm* — Morgan, Lewis & Bockius LLP

(57) ABSTRACT

A remedy for cancer obtained from a different viewpoint from the viewpoints employed in developing the existing anticancer drugs, i.e., focusing on the intercellular adhesion of cancer cells. Namely, provided is a remedy for cancer with fewer side effects which inhibits the proliferation of cancer cells and the intercellular adhesion of cancer cells. Also provided is an antibody, which recognizes the disintegrin domain of ADAM-15 and is usable as an anticancer agent, and so on. An antibody, which recognizes the disintegrin domain of ADAM-15 but does not recognize the RGD sequence or loop region in the disintegrin domain of ADAM-15, and so on; an antibody, which inhibits ADAM-15 and integrin αvβ3-dependent cell adhesion, and so on; and an antibody, which inhibits ADAM-15 and integrin αvβ1-dependent cell adhesion, and so on.

22 Claims, 10 Drawing Sheets

OTHER PUBLICATIONS

Nath et al. (1999) Interaction of metargidin (ADAM-15) with alpha-v-beta-3 and alpha-5-beta-1 integrins on different haemopoietic cells, J. Cell Sci. 112:579-587.

Tortorella et al. (1999) Purification and cloning of aggrecanase-1: a member of the ADAMTS family of proteins, Science 284:1664-1666.

Trochon-Joseph et al. (2004) Evidence of antiangiogenic and antimetastatic activities of the recombinant disintegrin domain of metargidin, Cancer Res. 64:2062-2069.

Wen et al. (1997) SUP-17, a *Caenorhabditis elegans* ADAM protein related to *Drosophila kuzbanian*, and its role in LIN-12/NOTCH signalling, Development 124:4759-4767.

Schutz, et al., "Expression of ADAM15 in Lung Carcinomas", Virchows Arch, 446, pp. 421-429, 2005.

Zhang, et al., "Specific Interaction of the Recombinant Disintegrin-like Domain of MDC-15 . . . ", J Biol Chem, 273, pp. 7345-7350, 1998.

Martin, et al., "The Role of ADAM 15 in Glomerular Mesangial Cell Migration", J Biol Chem, 277, pp. 33683-33689, 2002.

Eto, et al., "Functional Classification of ADAMs Based on a Conserved Motif . . . ", J Biol Chem, 277, pp. 17804-17810, 2002.

European Search Report mailed Nov. 7, 2011 in corresponding European application No. 09710825.2.

Charrier-Hisamuddin et al. ADAM-15: a metalloprotease that mediates inflammation. FASEB Journal. 22 641-653, 2007.

Charrier et al. ADAM-15 inhibits wound healing in human intestinal epithelial cell monolayers. Am J. Physiol Gastrointest Liver Physiol. 288 G346-G353, 2004.

* cited by examiner

[8F7 heavy chain]

```
ATGGGATGGAGTTGTATCATCCTCTTCTTGGTAGCAACAGCTACAGGTGTCCACTCCCAG
 M  G  W  S  C  I  I  L  F  L  V  A  T  A  T  G  V  H  S  Q
GTGCAACTGCAGCAGCCTGGGGCTGAGCTGGTGAAGCCTGGGGCCTCAGTGAAGGTGTCC
 V  Q  L  Q  Q  P  G  A  E  L  V  K  P  G  A  S  V  K  V  S
TGCAAGGCTTCTGCCTACACATTTACCAGTTACAATATGCACTGGGTAAAGCAGACACCT
 C  K  A  S  A  Y  T  F  T  S  Y  N  M  H  W  V  K  Q  T  P
GGACAGGGCCTGGAATGGATTGGAGCTATTTATCCAGGAGATGGTGATACTTCCTACAAT
 G  Q  G  L  E  W  I  G  A  I  Y  P  G  D  G  D  T  S  Y  N
CAGAAATTCAAAGGCAAGGCCACATTGACTGCAGACAAATCCTCCAGCACAGCCTACATT
 Q  K  F  K  G  K  A  T  L  T  A  D  K  S  S  S  T  A  Y  I
CATCTCAGCAGCCTGACATCTGAGGACTCTGCGGTCTATTACTGTGCAAGAGACAGGGGG
 H  L  S  S  L  T  S  E  D  S  A  V  Y  Y  C  A  R  D  R  G
GACTACGGCTACGGGTTTGCTTACTGGGGCCAAGGGACTCTGGTCACTGTCTCTGCAGCC
 D  Y  G  Y  G  F  A  Y  W  G  Q  G  T  L  V  T  V  S  A  A
AAAACGACACCCCCATCTGTCTATCCACTGGCCCCTGGATCTGCTGCCCAAACTAACTCC
 K  T  T  P  P  S  V  Y  P  L  A  P  G  S  A  A  Q  T  N  S
ATGGTGACCCTGGGATGCCTGGTCAAGGGCTATTTCCCTGAGCCAGTGACAGTGACCTGG
 M  V  T  L  G  C  L  V  K  G  Y  F  P  E  P  V  T  V  T  W
AACTCTGGATCCCTGTCCAGCGGTGTGCACACCTTCCCAGCTGTCCTGCAGTCTGACCTC
 N  S  G  S  L  S  S  G  V  H  T  F  P  A  V  L  Q  S  D  L
TACACTCTGAGCAGCTCAGTGACTGTCCCCTCCAGCACCTGGCCCAGCGAGACCGTCACC
 Y  T  L  S  S  S  V  T  V  P  S  S  T  W  P  S  E  T  V  T
TGCAACGTTGCCCACCCGGCCAGCAGCACCAAGGTGGACAAGAAAATTGTGCCCAGGGAT
 C  N  V  A  H  P  A  S  S  T  K  V  D  K  K  I  V  P  R  D
TGTGGTTGTAAGCCTTGCATATGTACAGTCCCAGAAGTATCATCTGTCTTCATCTTCCCC
 C  G  C  K  P  C  I  C  T  V  P  E  V  S  S  V  F  I  F  P
CCAAAGCCCAAGGATGTGCTCACCATTACTCTGACTCCTAAGGTCACGTGTGTTGTGGTA
 P  K  P  K  D  V  L  T  I  T  L  T  P  K  V  T  C  V  V  V
GACATCAGCAAGGATGATCCCGAGGTCCAGTTCAGCTGGTTTGTAGATGATGTGGAGGTG
 D  I  S  K  D  D  P  E  V  Q  F  S  W  F  V  D  D  V  E  V
CACACAGCTCAGACGCAACCCCGGGAGGAGCAGTTCAACAGCACTTTCCGCTCAGTCAGT
 H  T  A  Q  T  Q  P  R  E  E  Q  F  N  S  T  F  R  S  V  S
GAACTTCCCATCATGCACCAGGACTGGCTCAATGGCAAGGAGTTCAAATGCAGGGTCAAC
 E  L  P  I  M  H  Q  D  W  L  N  G  K  E  F  K  C  R  V  N
AGTGCAGCTTTCCCTGCCCCCATCGAGAAAACCATCTCCAAAACCAAAGGCAGACCGAAG
 S  A  A  F  P  A  P  I  E  K  T  I  S  K  T  K  G  R  P  K
GCTCCACAGGTGTACACCATTCCACCTCCCAAGGAGCAGATGGCCAAAGGATAA
 A  P  Q  V  Y  T  I  P  P  P  K  E  Q  M  A  K  G  *
```

Fig. 13

```
[8F7 light chain]
  ATGAAGTTGCCTGTTAGGCTGTTGGTGCTGATGTTCTGGATTCCTGCTTCCAGCAGTGAT
   M  K  L  P  V  R  L  L  V  L  M  F  W  I  P  A  S  S  S  D
  GTTGTGATGACCCAAACTCCACTCTCCCTGCCTGTCAGTCTTGGAGATCAAGCCTCCATC
   V  V  M  T  Q  T  P  L  S  L  P  V  S  L  G  D  Q  A  S  I
  TCTTGCAGATCTAGTCAGAGCCTTGTACACAGTAATGGAAACACCTATTTACATTGGTAC
   S  C  R  S  S  Q  S  L  V  H  S  N  G  N  T  Y  L  H  W  Y
  CTGCACAAGCCAGGCCAGTCTCCAAAGCTCCTGATCTACAAAGTTTCCAACCGATTTTCT
   L  H  K  P  G  Q  S  P  K  L  L  I  Y  K  V  S  N  R  F  S
  GGGGTCCCAGACAGGTTCAGTGGCAGTGGATCAGGGACAGATTTCACACTCAAGATCAGC
   G  V  P  D  R  F  S  G  S  G  S  G  T  D  F  T  L  K  I  S
  AGAGTGGAGGCTGAGGATCTGGGAGTTTATTTCTGCTCTCAAAATACACATGTTCCTCCG
   R  V  E  A  E  D  L  G  V  Y  F  C  S  Q  N  T  H  V  P  P
  TGGACGTTCGGTGGAGGCACCAAGCTGGAAATCAAACGGGCTGATGCTGCACCAACTGTA
   W  T  F  G  G  G  T  K  L  E  I  K  R  A  D  A  A  P  T  V
  TCCATCTTCCCACCATCCAGTGAGCAGTTAACATCTGGAGGTGCCTCAGTCGTGTGCTTC
   S  I  F  P  P  S  S  E  Q  L  T  S  G  G  A  S  V  V  C  F
  TTGAACAACTTCTACCCCAAAGACATCAATGTCAAGTGGAAGATTGATGGCAGTGAACGA
   L  N  N  F  Y  P  K  D  I  N  V  K  W  K  I  D  G  S  E  R
  CAAAATGGCGTCCTGAACAGTTGGACTGATCAGGACAGCAAAGACAGCACCTACAGCATG
   Q  N  G  V  L  N  S  W  T  D  Q  D  S  K  D  S  T  Y  S  M
  AGCAGCACCCTCACGTTGACCAAGGACGAGTATGAACGACATAACAGCTATACCTGTGAG
   S  S  T  L  T  L  T  K  D  E  Y  E  R  H  N  S  Y  T  C  E
  GCCACTCACAAGACATCAACTTCACCCATTGTCAAGAGCTTCAACAGGAATGAGTGTTAG
   A  T  H  K  T  S  T  S  P  I  V  K  S  F  N  R  N  E  C  *
```

ANTI-ADAM-15 ANTIBODIES AND UTILIZATION OF THE SAME

RELATED APPLICATIONS

The present application is a U.S. National Phase Application of International Application No. PCT/JP2009/052290 (filed Feb. 12, 2009) which claims priority to Japanese Patent Application No. 2008-033354 (filed Feb. 14, 2008) which are hereby incorporated by reference in their entirety.

SEQUENCE LISTING SUBMISSION VIA EFS-WEB

A computer readable text file, entitled "065393-5026-SequenceListing.txt," created on or about Aug. 11, 2010 with a file size of about 18 kb contains the sequence listing for this application and is hereby incorporated by reference in its entirety.

FIELD OF THE INVENTION

The present invention relates to an antibody that specifically recognizes ADAM-15 (A Disintegrin And Metalloprotease) or a fragment thereof (hereinafter, collectively referred to as an "antibody or the like"), DNA coding for the antibody or the like, a recombinant vector containing the DNA, a cell transformed with the vector, a cell that produces the antibody or the like, a method for producing the antibody or the like, a pharmaceutical composition containing the antibody or the like, and a diagnostic drug containing the antibody or the like. In addition, the present invention relates to a monoclonal antibody, a chimeric antibody, a humanized antibody and a human antibody that specifically recognize human ADAM-15, a hybridoma cell that produces the monoclonal antibody, a method for producing the monoclonal antibody, a method for producing the hybridoma cell, a therapeutic agent containing the antibody, a diagnostic agent containing the antibody, and the like.

BACKGROUND OF THE INVENTION

ADAM is a cysteine-rich molecule consisting of a disintegrin domain and a metalloprotease-like domain, which has been receiving much attention since it is a functional protein that not only exhibits metalloproteinase activity but also has adhesive activity. Most of ADAMs have transmembrane domains and localized in the cell membrane, thereby playing an extremely important role in molecular regulation on the cell surface. So far, 30 or more ADAM family proteins have been identified. Since the extracellular portion of ADAMs is involved in cell adhesion, cell fusion, proteolysis and intracellular signaling, they are implicated in fertilization, neurogenesis, myoblast fusion and cleavage of cytokines. In particular, since ADAM family proteins are membrane-anchored proteins that have similar structure to snake venom disintegrin, they are involved in various biological processes involving cell-to-cell and cell-to-matrix interactions (for example, fertilization, muscle development, neurogenesis and the like). Thus far, intensive research has been made on the search of novel ADAM molecule, clarification of their functions and methods for regulating them with the intention of drug discovery.

For example, ADAM-1 and ADAM-2 are believed to be involved in fertilization between egg and sperm via egg integrin (see Non-Patent Publication 1). ADAM-10 is suggested to be involved in control of Notch signal and plays an important role in neurogenesis, in processing of membrane protein and further in degradation of extracellular matrix component (see Non-Patent Publication 2). Recently, one type of aggrecanase which had been considered to be a degradative enzyme of aggrecan, i.e., a cartilage extracellular matrix, was purified and cloned, and reported to be a molecule of the ADAM family (see Non-Patent Publication 3). Therefore, development of a therapeutic drug for arthritis or osteoarthritis can be expected by regulating the enzyme activity of ADAM-10. ADAM-13 is expressed in *xenopus laevis* during embryogenesis, and considered to play an important role in its morphogenesis (see Non-Patent Publication 4). At this point, mammal-derived ADAM-13 has not been reported. ADAM-17 is known as a tumor necrosis factor (TNF) convertase (a synthase of soluble TNF). ADAM-17 inhibitors have been studied enthusiastically as prophylactic and/or therapeutic drugs for disorders caused by abnormal increase of TNF (inflammation, fever, malfunction of the circulatory system, graft-versus-host reaction, autoimmune disorder or the like). Methods for screening ADAM-17 itself and an ADAM-17 inhibitor have already been disclosed (see Patent Publications 1 and 2).

ADAM-15 is a transmembrane glycoprotein with a molecular weight of about 90 KDa that belongs to the ADAM family proteins. ADAM-15 has been found to have a function as an adhesion molecule involved in cell-to-cell adhesion via its disintegrin domain (see Non-Patent Publication 5). Among 20 or more ADAM family proteins, only human ADAM-15 has a RGD tripeptide sequence in the disintegrin domain, and specific interaction between recombinant human ADAM-15 and integrin $\alpha v \beta 3$ is suggested to depend on the RGD sequence. ADAM-15 has been suggested of its interaction with integrins ($\alpha v \beta 3$, $\alpha 5 \beta 1$, $\alpha II \beta 3$, $\alpha 9 \beta 1$) and possible involvement in cell-to-cell adhesion. Moreover, ADAM-15 in which R481, C487, D488, L489, P490, E491 and/or F492 among the amino acids 481-492 (RPTRGDCDLPEF) (loop sequence) including the RGD sequence of the disintegrin domain has been substituted with alanine, has decreased interaction ability with $\alpha 9 \beta 1$ integrin. Thus, R481, C487, D488, L489, P490, E491 and/or F492 of ADAM-15 are/is shown to be necessary for the interaction between ADAM-15 and $\alpha 9 \beta 1$ integrin (see Non-Patent Publication 6).

Since administration of recombinant ADAM-15 disintegrin domain inhibits proliferation of breast cancer cells, interaction between ADAM-15 and integrin appears to concern proliferation of cancer cells (see Non-Patent Publication 7).

ADAM-15 is also considered to be relevant to cell migration. For example, migration is reported to be reduced in NIH3T3 cell overexpressing ADAM-15 (see Non-Patent Publication 8). Additionally, overexpression of ADAM-15 in Jurkat cell is reported to enhance cell aggregation (see Non-Patent Publication 9). Moreover, ADAM-15 is reported to co-localize with a cell adhesion molecule VE cadherin (see Non-Patent Publication 10). Accordingly, ADAM-15 is considered to have an important role in cell-to-cell adhesion.

ADAM-15 is expressed in any body tissues as well as in vascular endothelial cells, and angiogenesis is reported to be suppressed in ADAM-15-knockout mice (see Non-Patent Publication 11). Furthermore, since stimulation of HUVEC with VEGF enhances expression of VEGFR-2 and ADAM-15, association between ADAM-15 and angiogenesis has been suggested (see Non-Patent Publication 12).

Since cell proliferation, cell migration, cell-to-cell adhesion and angiogenesis that have been reported of their connection with ADAM-15 are closely related to cancer and metastasis of cancer, ADAM-15 seems to be responsible for cancer and metastasis of cancer.

Since ADAM-15 expression is enhanced in rheumatoid arthritis, arteriosclerosis or the like, it also seems to be responsible for the process of tissue repair. Since ADAM-15 expression is also enhanced in the infarction site and the non-infarction site during the early phase of myocardial infarction, it seems to be responsible for the process of tissue repair in the heart.

However, no detailed report has been given on the association between the structure of ADAM-15 and these diverse functions of ADAM-15, and as to which component is exerting the functions of ADAM-15 has been unknown.

Monoclonal antibodies for ADAM-15, for example, 23G9 sold by R & D or the like are known but the relationship between these antibodies and the functions of ADAM-15 has not been reported. Moreover, there has been no report of an antibody that recognizes the ADAM-15 disintegrin domain.

Currently, although many drugs are known as therapeutic drugs for cancer, most of them have strong side-effects and thus development of a prophylactic drug and/or a therapeutic drug for cancer that is therapeutically effective with less side-effect has been anticipated. Previous antitumor agents have been developed to be drugs with less side-effect that can treat cancer by exerting specific cytocidal effect or cytostatic effect against cancer cells. In fact, however, most of these drugs also act on normal cells, causing severe side-effects.

[Patent Reference 1] U.S. Pat. No. 5,830,742
[Patent Publication 2] U.S. Pat. No. 6,013,466
[Non-Patent Publication 1] Almeida, E. A. et al., Cell, 81, 1095-1104, 1995
[Non-Patent Publication 2] Wen, C. et al., Development, 124, 4759-4767, 1997
[Non-Patent Publication 3] Tortorella, M. D. et al., Science, 284, 1664-1666, 1999
[Non-Patent Publication 4] Alfandari, D. et al., Dev. Biol., 182, 314-330, 1997
[Non-Patent Publication 5] Zhang, X. P. et al., J. Biol. Chem. 273, 7345-7350, 1998;
[Non-Patent Publication 6] Nath, D. et al., J. Cell Sci. 112, 579-587, 1999 P. 468-473.
[Non-Patent Publication 7] Eto, K. et al. J. Biol. Chem. 277, 17804-17810, 2002
[Non-Patent Publication 8] Trochon-Joseph, V., et al., Cancer Res, 64, 2062-2069, 2004
[Non-Patent Publication 9] Herren, B., et al., Exp Cell Res, 271, 152-160, 2001
[Non-Patent Publication 10] Charrier, L., et al., J Biol Chem, 282, 16948-16958, 2007
[Non-Patent Publication 11] Ham, C., et al., Exp Cell Res, 279, 239-247, 2002
[Non-Patent Publication 12] Horiuchi, K., et al., Mol Cell Biol, 23, 5614-5624, 2003
[Non-Patent Publication 13] Komiya, K., et al., Arthritis Res Ther, 7, R1158-1173, 2005

DISCLOSURE OF THE INVENTION

Problems to be Solved by the Invention

The present invention has an objective of providing a therapeutic drug for cancer from a different perspective from conventional antitumor agent development in that focus is placed on cell-to-cell adhesion of the cancer cells. Specifically, the present invention has an objective of providing a therapeutic drug for cancer that can suppress proliferation and cell-to-cell adhesion of a cancer cell with less side-effect. Additionally, the present invention has an objective of providing an antibody available as an antitumor agent that recognizes the ADAM-15 disintegrin domain.

Means for Solving the Problems

The present inventors have gone through keen examination on antibodies that recognize ADAM-15, and found that an antibody that recognizes the ADAM-15 disintegrin domain has a cytostatic effect on cancer cells and a cell adhesion inhibitory effect. The present inventors considered that the cytostatic effect on cancer cells and the cell adhesion inhibitory effect of this antibody are exerted upon inhibition of binding between ADAM-15 and integrin. By carrying out further study, the inventors have surprisingly found that this antibody does not recognize the RGD sequence and the loop sequence in the disintegrin domain that has conventionally been believed to be the integrin-binding site of ADAM-15. Based on these study achievements, the present inventors found that an antibody that recognizes a site different from the conventionally-known integrin-binding site of ADAM-15 has a cytostatic effect on cancer cells and a cell adhesion inhibitory effect, thereby accomplishing the present invention.

Thus, the present invention provides an antibody or the like that specifically recognizes ADAM-15, DNA coding for the antibody or the like, a recombinant vector comprising the DNA, a cell transformed with the vector, a cell that produces the antibody or the like, a method for producing the antibody or the like, a pharmaceutical composition comprising the antibody or the like, and a diagnostic drug comprising the antibody or the like recited below.

(1) An antibody or a fragment thereof that recognizes ADAM-15 disintegrin domain, but that does not recognize RGD sequence in the ADAM-15 disintegrin domain.

(2) An antibody or a fragment thereof that recognizes ADAM-15 disintegrin domain, but that does not recognize loop region in the ADAM-15 disintegrin domain.

(3) The antibody or the fragment thereof according to (1) or (2) above, which inhibits ADAM-15 and integrin αvβ3-dependent cell adhesion.

(4) The antibody or the fragment thereof according to any one of (1) to (3) above, which inhibits ADAM-15 and integrin α9β1-dependent cell adhesion.

(5) The antibody or the fragment thereof according to any one of (1) to (4) above, characterized by suppressing proliferation of a cancer cell.

(6) The antibody or the fragment thereof according to any one of (1) to (5) above, wherein the antibody is a monoclonal antibody.

(7) The antibody or the fragment thereof according to any one of (1) to (6) above, wherein the antibody comprises a heavy chain having the amino acid sequence represented by SEQ ID NO:12 and/or a light chain having the amino acid sequence represented by SEQ ID NO:14.

(8) The antibody or the fragment thereof according to (6) above, wherein the antibody is a monoclonal antibody produced by a hybridoma cell defined by Accession No. FERM ABP-10950.

(9) The antibody or the fragment thereof according to any one of (1) to (7) above, wherein the antibody is a chimeric antibody, a humanized antibody or a human antibody.

(10) The antibody or the fragment thereof according to any one of (1) to (5) above, wherein the antibody fragment is F(ab')$_2$, Fab', Fab, single-chain Fv (scFv), disulfide-linked Fv (dsFv), a polymer thereof or dimeric V region (diabody).

(11) The antibody or the fragment thereof according to any one of (1) to (5) above, wherein the antibody fragment is a peptide comprising the CDR sequence of the antibody.

(12) The antibody or the fragment thereof according to (11) above, wherein the CDR sequence comprises the amino acid sequence represented by SEQ ID NO:15, 16, 17, 18, 19 or 20.

(13) DNA coding for the antibody or the fragment thereof according to any one of (1) to (12) above.

(14) A recombinant vector comprising the DNA according to (13) above.

(15) A transformed cell obtained by introducing the recombinant vector according to (14) above into a host cell.

(16) The cell according to (15) above which is a hybridoma cell line.

(17) The cell according to (16) above which is a hybridoma cell line defined by Accession No. FERM ABP-10950.

(18) A method for producing the antibody or the fragment thereof according to any one of (1) to (12) above, the method comprising the steps of: culturing the cell according to (15) or (16) above; growing the antibody or the fragment thereof in the culture; and extracting the antibody or the fragment thereof from the culture.

(19) A pharmaceutical composition comprising the antibody or the fragment thereof according to any one of (1) to (12) above as an active element.

(20) The pharmaceutical composition according to (19) above, which is a therapeutic drug or a prophylactic drug for a disease caused by cell proliferation, cell migration, cell-to-cell adhesion or angiogenesis.

(21) The pharmaceutical composition according to (19) above, which is an antitumor agent or a metastasis-suppressing agent for cancer.

(22) A diagnostic drug comprising the antibody or the fragment thereof according to any one of (1) to (12) above.

(23) The diagnostic drug according to (22) above, which is a diagnostic drug for a disease caused by cell proliferation, cell migration, cell-to-cell adhesion or angiogenesis.

Effect of the Invention

Since an anti-ADAM-15 antibody or the like of the present invention shows superior suppressive action against ADAM-15 functions, it is considered therapeutically effective against diseases caused by cell proliferation, cell migration, cell-to-cell adhesion or angiogenesis. Hence, the antibody or the like of the present invention is therapeutically effective against cancers (for example, proliferation of cancer cells, metastasis), inflammatory diseases (for example, rheumatoid arthritis, osteoarthritis, hepatitis, bronchial asthma, fibrosis, diabetes, arteriosclerosis, multiple sclerosis, inflammatory bowel diseases (ulcerative colitis, Crohn's disease, etc.)), infectious diseases (for example, hepatitis), autoimmune disorders (for example, systemic lupus erythematosus, polymyositis, autoimmune thyroid disease, tubulointerstitial nephritis, myasthenia gravis), skeletal diseases (for example, osteoporosis) and the like. In addition, the antibody of the present invention is capable of histologically detecting ADAM-15 expression in a cell or a tissue.

BEST MODES FOR CARRYING OUT THE INVENTION

According to one embodiment of the present invention, there is provided an antibody or the like that binds to ADAM-15 but that does not recognize the RGD sequence in the ADAM-15 disintegrin domain, and an antibody or the like that binds to ADAM-15 but that does not recognize the loop region in the ADAM-15 disintegrin domain.

The antibody or the like of the present invention may bind to (or recognize) a substance other than ADAM-15 as long as it is usable as an antibody or the like of the present invention, but preferably it specifically binds to (or recognizes) ADAM-15. Herein, when an antibody "specifically binds to (or recognizes)" a certain protein or a fragment thereof, it means that the antibody binds to a particular amino acid sequence of the certain protein or the fragment thereof with substantially higher affinity than affinity to other amino acid sequence. Herein, the phrase "substantially high affinity" refers to an affinity level of a particular amino acid sequence which is distinguishable from a level of other amino acid sequence when detected with an intended measurement device or method. The association constant ($K_a$) of binding with substantially high affinity is, for example, at least $10^7 M^{-1}$, preferably at least $10^8 M^{-1}$, and more preferably at least $10^9 M^{-1}$. Still more preferable association constant is $10^{10} M^{-1}$, $10^{11} M^{-1}$, $10^{12} M^{-1}$ or higher, for example $10^{13} M^{-1}$ or higher.

ADAM-15 recognized by an antibody or the like of the present invention is preferably, but without limitation, ADAM-15 of a mammal such as a mouse, a rat, a hamster, a rabbit or a human, and more preferably human ADAM-15. Information of the amino acid sequences of these ADAM-15 and the nucleotide sequences encoding them is publicly available from a gene sequence database such as GenBank (for example, GeneIDs: 8751 (*Homosapiens*), 11490 (*Mus musculus*), 57025 (*Rattus norvegicus*), etc.).

ADAM-15 recognized by an antibody or the like of the present invention also comprises a polypeptide that has substantially the same amino acid sequence as ADAM-15. Herein, a "polypeptide having substantially the same amino acid sequence" refers to a mutant polypeptide that has substantially equivalent biological property to naturally-occurring ADAM-15, preferably human ADAM-15, and having an amino acid sequence in which one or more amino acids, preferably 1-10 amino acids, more preferably one to several (for example, 1-5, 1-4, 1-3 or 1-2) amino acids have been substituted, deleted and/or inserted, or a mutant polypeptide that has substantially equivalent biological property to naturally-occurring ADAM-15, preferably human ADAM-15, and having an amino acid sequence in which one or more amino acids, preferably 1-10 amino acids, more preferably one to several (for example, 1-5, 1-4, 1-3 or 1-2) amino acids are added to the amino acid sequence of the naturally-occurring ADAM-15, preferably human ADAM-15. Furthermore, a polypeptide having substantially the same amino acid sequence as ADAM-15 may be a mutant polypeptide having two or more of the above-described substitution, deletion, insertion and addition.

According to another embodiment of the present invention, there are provided an antibody or the like that recognizes ADAM-15, and that inhibits ADAM-15 and integrin αvβ3-dependent cell adhesion, or that inhibits ADAM-15 and integrin α9β1-dependent cell adhesion. ADAM-15 and integrin may be expressed on the same cell surface or on different cell surfaces, but preferably they are expressed on different cell surfaces.

The antibody of the present invention may be either a polyclonal antibody or a monoclonal antibody, but it is preferably a monoclonal antibody. According to the present invention, a "monoclonal antibody" is highly specific to an antigen and recognizes a single antigen.

Furthermore, the antibody of the present invention comprises a nonhuman animal antibody, an antibody having an amino acid sequence of a nonhuman animal antibody and an amino acid sequence of a human-derived antibody, and a human antibody. Examples of nonhuman animal antibodies include antibodies from a mouse, a rat, a hamster, a guinea pig, a rabbit, a dog, a monkey, a sheep, a goat, a chicken, a duck and the like, preferably antibodies from animals which can produce a hybridoma, and more preferably an antibody from a mouse. Examples of antibodies having an amino acid sequence of a nonhuman animal antibody and an amino acid sequence of a human-derived antibody include a human chimeric antibody and a humanized antibody. In the above description, the term "chimeric antibody" refers to a genetically engineered antibody in which a constant region of an anti-ADAM-15 antibody from a nonhuman animal is modified to have the same constant region as that of a human antibody, and it is preferably a human-mouse chimeric antibody (see European Patent Publication No. EP0125023). The term "a humanized antibody" refers to a genetically engineered antibody in which the primary structure of nonhuman animal-derived anti-human ADAM-15 antibody except for the complementary determining regions (CDRs) of the H- and L-chains is modified to have the primary structure corresponding to that of a human antibody. Herein, "CDR" is as defined by Kabat et al. ("Sequences of Proteins of Immunological Interest", Kabat, E. et al., U.S. Department of Health and Human Services, 1983) or Chothia et al. (Chothia & Lesk, J. Mol. Biol., 196, 901-917, 1987). The term "human antibody" is an expression product of a completely human-derived antibody gene, examples including a monoclonal antibody prepared by using a transgenic animal introduced with a gene associated with human antibody production (see European Patent Publication No. EP0546073) and the like. When the subject of the treatment is human, and the ADAM-15 antibody producing animal is a mouse, it is preferably a human-mouse chimeric antibody or a humanized antibody, and more preferably a human monoclonal antibody.

The immunoglobulin class of an antibody of the present invention is not particularly limited and may be any of the immunoglobulin classes IgG, IgM, IgA, IgE, IgD and IgY. An antibody of the present invention comprises antibodies of any isotypes.

In another embodiment of the present invention, there is provided a fragment of the anti-ADAM-15 antibody. Herein, the term "antibody fragment" refers to a part of the antibody (e.g., a domain), which retains the ability of the antibody to act toward an antigen (e.g., binding ability, neutralizing ability). Examples of such antibody fragments include: F(ab')$_2$, Fab', Fab, single-chain Fv (hereinafter, referred to as "scFv"), disulfide-linked Fv (hereinafter, referred to as "dsFv"), a polymer thereof, dimeric V region (hereinafter, referred to as a "diabody"), and peptides containing CDR. F(ab')$_2$ is an antibody fragment with a molecular weight of about 100,000 having antigen-binding activity among the fragment obtained by treating IgG with proteolysis enzyme pepsin. Fab' is an antibody fragment with a molecular weight of about 50,000 having antigen-binding activity which is obtained by cleaving the disulfide binding at the hinge region of F(ab'). sdFv is a polypeptide having an antigen-binding activity, in which a single VH and a single VL are linked via a peptide linker. dsFv is a fragment having an antigen-binding activity, in which amino acid residues substituted with cysteine residues in VH and VL are bound via a disulfide binding. A diabody is a dimeric fragment of scFvs. The diabody of the present invention may be either monospecific or bispecific (multispecific antibody). The dimerized scFvs may be either identical or different.

The fragment of the antibody of the present invention also comprises a peptide containing a part of the anti-ADAM-15 antibody. Herein, the phrase "peptide containing a part of an antibody" refers to a peptide comprising a part of the amino acid sequence constituting the antibody, and retaining the ability of the antibody to act toward an antigen (e.g., binding ability, neutralizing ability). The peptide containing a part of the antibody may comprise an amino acid sequence that is not derived from that antibody. The peptide containing a part of the anti-ADAM-15 antibody is preferably a peptide containing a CDR sequence of the anti-ADAM-15 antibody. Herein, the peptide containing a CDR sequence is a peptide containing an amino acid sequence of at least one CDR selected from CDR1, CDR2 and CDR3 of the heavy chain variable region and CDR1, CDR2 and CDR3 of the light chain variable region. More preferably, the peptide containing a part of the anti-ADAM-15 antibody is a peptide containing an amino acid sequence of CDR3 of heavy chain variable region and/or CDR3 of light chain variable region.

Representative examples of heavy and light chains of the anti-ADAM-15 antibody of the present invention have the amino acid sequences represented by SEQ ID NOS:12 and 14, respectively. Moreover, representative examples of CDR1, CDR2 and CDR3 of the heavy chain variable region and CDR1, CDR2 and CDR3 of the light chain variable region of the anti-ADAM-15 antibody have the amino acid sequences represented by SEQ ID NOS:15, 16 and 17 and SEQ ID NOS:18, 19 and 20, respectively.

Since the antibody of the present invention inhibits the functions of ADAM-15, it may be used as a therapeutic or prophylactic drug for ADAM-15-associated diseases. Herein, "ADAM-15-associated diseases" refer to diseases caused by cell proliferation, cell migration, cell infiltration, cell-to-cell adhesion or angiogenesis, examples of such diseases including cancers (esophagus cancer, thyroid cancer, bladder cancer, colorectal cancer, gastric cancer, pancreatic cancer, thoractic cancer, liver cancer, lung cancer, breast cancer, neuroblastoma, glioblastoma, uterus cancer, ovary cancer, prostate cancer, Wilms' tumor) and metastases thereof, diseases caused by cell proliferation or angiogenesis such as endometriosis; arthritis, infectious diseases (hepatitis, etc.), bronchial asthma, fibrosis, autoimmune disorders (for example, systemic lupus erythematosus (SLE), polymyositis (PM), autoimmune thyroid disease, tubulointerstitial nephritis, myasthenia gravis (EAMG), organ-specific autoimmune disorder, etc.), rheumatic arthritides (chronic rheumatoid arthritis (RA), osteoarthritis (OA)), multiple sclerosis (relapsing-remitting multiple sclerosis, etc.), inflammatory enterocolitis (ulcerative colitis, Crohn's disease, etc.), progressive systemic sclerosis (PSS), Sjogren's syndrome, dermatomyositis (DM), periarteritis nodosa (PN), thyroid diseases (Grave's disease, etc.), Guillain-Barre syndrome, primary biliary cirrhosis (PBC), idiopathic thrombocytopenic purpura, autoimmune hemolytic anemia, amyotrophic lateral sclerosis (ALS), type I diabetes, transplant rejection, adhesions after operation, endometriosis, psoriasis, lupus, allergy, asthma, diseases caused by inflammatory diseases or cell migration such as abnormal neutrophil function; occlusive vascular diseases such as restenosis after revascularization, heart coronary occlusive vascular disease, brain occlusive vascular disease, kidney occlusive vascular disease, peripheral occlusive vascular disease, arteriosclerosis and cerebral infarction, and diseases caused by intimal hypertrophy. Preferably, ADAM-15-associated disease according to the present invention is cancer.

An antibody of the present invention may be used as a diagnostic drug for an ADAM-15-associated disease. When the antibody is used as a diagnostic drug, the antibody or the fragment thereof used desirably recognizes ADAM-15 in a specific manner.

1. Preparation of Anti-ADAM-15 Antibody

An antibody of the present invention may be prepared, for example, by immunizing a nonhuman mammal or avian with ADAM-15 or a peptide having a part of ADAM-15 and if necessary an immunostimulant (for example, mineral oil or aluminum precipitate and heat-killed bacteria or lipopolysaccharide, complete Freund's adjuvant or incomplete Freund's adjuvant, etc.).

ADAM-15 used as an immunogen is preferably mammal ADAM-15, and particularly preferably human ADAM-15. ADAM-15 that is used as an antigen of the present invention may be obtained as: (1) any cells expressing ADAM-15 of human or other mammal, or a protein derived from any tissues containing such a cell; (2) a recombinant protein expressed by introducing gene DNA, preferably cDNA, coding for ADAM-15 into a cell line such as a bacterium, an yeast or an animal cell; or (3) a synthetic protein.

An immunogen used for preparing an antibody of the present invention can be obtained, for example, by introducing an expression vector containing cDNA coding for ADAM-15 into $E.\ coli$, an yeast, an insect cell, an animal cell or the like for expression. As an immunogen used for preparing an antibody of the present invention, for example, a cell overexpressing ADAM-15 on the cell membrane may be used per se. As an immunogen used for preparing an antibody of the present invention, for example, a membrane fraction of a cell expressing ADAM-15 may also be used. A cell overexpressing ADAM-15 on the cell membrane may be obtained by cloning a gene (e.g., cDNA) encoding ADAM-15 by a known genetic engineering technique for overexpression of ADAM-15 on the cell membrane. A membrane fraction of the cell overexpressing ADAM-15 on the cell membrane may be obtained by disrupting the cell expressing (preferably the cell overexpressing) ADAM-15 and extracting the membrane fraction thereof.

When a peptide having a part of ADAM-15 is used as an immunogen, it can be obtained by introducing an expression vector containing cDNA coding for such a peptide into $E.\ coli$, an yeast, an insect cell, an animal cell or the like for expression. The peptide containing a part of ADAM-15 is preferably a peptide containing the loop region of ADAM-15.

Furthermore, ADAM-15 or a peptide having a part of ADAM-15 may be prepared by chemical synthesis using Fmoc method or Boc method. For example, an amino acid at the C-terminal of ADAM-15 or a peptide having a part of ADAM-15 is immobilized onto an polystyrene carrier, and caused to react with and bind to an amino acid protected by a 9-fluorenylmethyloxycarbonyl group (Fmoc group) or a tert-butoxycarbonyl group (Boc group) by using a condensation agent such as diisopropylcarbodiimide (DIC), followed by rounds of washing and deprotection steps, thereby obtaining a peptide having the intended amino acid sequence.

Alternatively, ADAM-15 or a peptide having a part of ADAM-15 may be synthesized with an automatic peptide synthesizer. Examples of such peptide synthesizers include PSSM-8 (Shimadzu Co.); Model 433A peptide synthesizer (Applied Biosystems, Inc.); and ACT396Apex (Advanced ChemTech Inc.).

Examples of methods for producing a polypeptide having substantially the same amino acid sequence as ADAM-15 include site-directed mutagenesis using synthetic oligonucleotide (gapped duplex method), random point mutagenesis by nitrous acid or sulfurous acid treatment, a method for preparing a deficient mutant with Ba131 enzyme or the like, cassette mutagenesis, linker scanning method, misincorporation method, mismatch primer method, and DNA segment synthesis method.

The immunogen is administered alone or together with a carrier or a diluent to a site of an immunized animal where an antibody can be produced upon administration. Upon administration, a complete Freund's adjuvant or an incomplete Freund's adjuvant may be administered in order to enhance the antibody production capacity.

The animal to be immunized is not particularly limited as long as it is capable of producing a hybridoma, such as a mouse, a rat, a hamster, a guinea pig, a rabbit, a dog, a monkey, a sheep, a goat, a chicken or a duck, but preferably a mouse or a rat, and more preferably a mouse.

Administration of the immunogen to the animal may be carried out, for example, by subcutaneous injection, intraperitoneal injection, intravenous injection, intradermal injection, intramuscular injection or footpad injection, but preferably subcutaneous injection or intraperitoneal injection. The amount of the immunogen used is not particularly limited as long as the antibody is produced, but it is preferably 0.1 to 1000 µg, more preferably 1 to 500 µg, and still more preferably 10 to 100 µg. Immunization may be carried out once or several times at appropriate intervals. Generally, immunization takes place once in every 1 to 6 weeks for a total of about 2 to 10 times, preferably once every 1 to 5 weeks for a total of 2 to 5 times, and more preferably once every 3 weeks for a total of 3 times. One to two weeks following the last immunization, blood is drawn from the orbit or the tail vein of the immunized animal and the serum is used to measure the antibody titer. An antibody titer may be measured according to a method known to those skilled in the art. Examples of such methods include radioimmuno assay (RIA), solid phase enzyme-linked immunosorbent assay (ELISA), fluorescent antibody technique and passive hemagglutination assay, but preferably ELISA. An antibody of the present invention may be obtained by purification from a serum of an animal exhibiting sufficient antibody titer.

A monoclonal antibody of the present invention may be obtained by culturing a hybridoma obtained by fusing the antibody-producing cell from the animal immunized according to the above-mentioned method with a myeloma cell. An example of such a fusion method includes a method by Milstein et al. (Galfre, G. & Milstein, C., Methods Enzymol. 73:3-46, 1981).

The antibody-producing cell used may be collected from spleen, pancreas, lymph nodes, peripheral blood, preferably spleen, of a mouse or a rat immunized according to the above-mentioned method and whose serum is exhibiting sufficient antibody titer.

The myeloma cell used, for example, is a cell derived from a mammal such as a mouse, a rat, a guinea pig, a hamster, a rabbit or a human, but not particularly limited as long as it is capable of in vitro proliferation. Examples of such cells include P3-X63Ag8 (X63) (Nature, 256, 495, 1975), P3/NS1/1-Ag4-1 (NS1) (Eur. J. Immunol., 6, 292, 1976), P3X63Ag8U1 (P3U1) (Curr. Top. Microbiol. Immunol., 81, 1, 1978), P3X63Ag8. 653 (653) (J. Immunol., 123, 1548, 1979), Sp2/0-Ag14 (Sp2/O) (Nature, 276, 269, 1978), and Sp2/O/FO-2 (FO-2) (J. Immunol. Methods, 35, 1, 1980), preferably a cell derived from an animal of the same species as that of the antibody-producing cell, and more preferably a cell derived from an animal of the same line as that of the antibody-producing cell. For example, a mouse-derived myeloma cell is preferably P3U1 or P3X63-Ag8-653. The myeloma cell is frozen for preservation, or maintained by passage culture in a common medium supplemented with horse, rabbit or fetal bovine serum. Additionally, the myeloma cell used for cell fusion is preferably a cell in the logarithmic growing phase.

Examples of a method for forming a hybridoma by fusing the antibody-producing cell and a myeloma cell include a method using polyethylene glycol (hereinafter, referred to as "PEG") or the like (PEG method), a method using Sendai virus, and a method employing an electrofusion device.

In the case of PEG method, for example, the antibody-producing cell obtained by the above-mentioned method and the myeloma cell are washed with a medium, PBS (Phosphate Buffered Saline) or the like. Subsequently, a spleen cell and the myeloma cell are suspended in an appropriate medium or buffer containing a cell aggregative vehicle such as 30 to 60% PEG (average molecular weight: 1000 to 6000) at a mix ratio of 1:2 to 10:1 (preferably, 5:1 to 10:1) and allowed to react under the conditions at a temperature of about 25 to 37° C. at pH 6 to 8 for about 30 seconds to 3 minutes (Elsevier Publishing, 1988). At the end of the reaction, PEG solution is removed and the resultant is resuspended in the medium and seeded onto a cell well plate for continued culture.

Screening of the hybridoma cells producing the monoclonal antibody may be carried out according to a known method or a method based thereon. In general, hybridoma cells can be screened by selective proliferation with a medium for animal cells supplemented with HAT (Hypoxanthine-aminopterin-thymidine). Media for screening and culture may be any media as long as they allow the growth of the hybridoma cells. For example, a RPMI1640 medium containing 1 to 20%, preferably 10 to 20% fetal bovine serum, a GIT medium containing 1 to 10% fetal bovine serum (Wako Pure Chemical Industries, Ltd.), a serum-free medium for hybridoma culture (SFM-101, Nissui Pharmaceutical Co., Ltd.) or the like may be used. Culture temperature is usually 20 to 40° C., preferably about 37° C. Culture time is usually 5 days to 3 weeks, preferably 1 to 2 weeks. Culture may generally be performed in 5% $CO_2$.

Following cultivation, the culture supernatant is collected, allowed to bind to the antigen protein by ELISA or the like to select samples that do not bind with non-antigen proteins. Confirmation and screening may be conducted, for example, by employing cellular ELISA described in "New Clinical Immuno Experiment Procedures (*Shin Rinsho Men-eki Jikken Sosa-Hou*)" (part 3) (Kagaku Hyouron-sha, 1997). Limiting dilution is repeated for 1 to 5 times, preferably 2 to 4 times to obtain a single type of cells from such clones, thereby selecting cells that are stably exhibiting high antibody titer.

The monoclonal antibody of the present invention may be obtained by culturing the hybridoma obtained by the above-described method in vitro and purifying the culture solution. The monoclonal antibody of the present invention may also be obtained by: transplanting the hybridoma into an inbred animal or an immunocompromised animal that has been intraperitoneally administered with pristane; producing ascites therefrom; and purifying the collected ascites.

The resulting antibody may be purified to homogeneity. For separation/purification of the antibody, a separation/purification method employed for common proteins may be employed. The antibody may be separated/purified for example, by appropriately selecting and combining a chromatography column such as affinity chromatography, a filter, ultrafiltration, salting-out, dialysis, SDS polyacrylamide gel electrophoresis, isoelectric electrophoresis or the like (Antibodies: A Laboratory Manual. Ed Harlow and David Lane, Cold Spring Harbor Laboratory, 1988). Examples of columns used for affinity chromatography include a protein A column and a protein G column. Examples of protein A columns include Hyper D, POROS and Sepharose F. F. (Amersham Biosciences). In the case of IgY and IgM, a column using mercaptopyridine as a ligand may be used. Additionally, an ADAM-15-immobilized column, ion-exchange chromatography, hydrophobic interaction chromatography or the like may also be used regardless of the antibody class. A monoclonal antibody may be purified, for example, by centrifugation and subsequent collection of the IgG fraction by using a protein A column, a protein G column or the like.

2. Preparation of Human Chimeric Antibody, Humanized Antibody and Human Antibody (1) Human Chimeric Antibody A human chimeric antibody of the present invention may be obtained by the steps of: preparing DNA coding for VH and VL of a nonhuman animal-derived monoclonal antibody that binds to ADAM-15 and inhibits the functions thereof; binding the DNA with constant region cDNA of a human-derived immunoglobulin for incorporation into an expression vector; and introducing the vector into an appropriate host cell for expression (Morrison, S. L. et al., Proc. Natl. Acad. Sci. USA, 81, 6851-6855, 1984).

DNAs coding for VH and VL of the nonhuman animal-derived monoclonal antibody may be obtained, for example, according to the following method. mRNA is extracted from an animal B cell producing this monoclonal antibody. Extraction of mRNA may be carried out according to a method well known to those skilled in the art. For example, RNA may be prepared by guanidine-ultracentrifugation method (Chirgwin, J. M. et al., Biochemistry, 18, 5294-5299, 1979), AGPC method (Chomczynski, P et al., Analytical Biochemistry, 162, 156-159, 1987) or the like, and purified with mRNA Purification Kit (Pharmacia, Takara Bio) or the like. cDNA is prepared from the extracted mRNA by using oligo dT primers and integrated into a vector. cDNA encoding the nonhuman animal-derived monoclonal antibody is isolated from the cDNA integrated into the vector by using a part of the non-human animal-derived monoclonal antibody as a probe. The nucleotide sequence of the isolated cDNA is determined to obtain DNA sequences coding for VH and VL of interest.

Moreover, another method for obtaining DNAs coding for VH and VL of the nonhuman animal-derived monoclonal antibody is as follows. The cDNA obtained by the above-described method is amplified by PCR method with primers capable of amplifying VH or VL (for example, in the case where a mouse is used as the nonhuman animal, a primer that hybridizes with the mouse H-chain constant region (C region) and a primer that hybridizes with the conserved sequence of the mouse gamma light chain constant region (R. Orlandi et al., Proc. Natl. Acad. Sci. USA, 86, 3833, 1989)), or mRNA is extracted from the animal B cell that produces the mono-clonal antibody and VH or VL is amplified by RT-PCR method with primers capable of amplifying the VH or VL. The DNA fragment of interest is extracted from the resulting PCR product. Extraction of the DNA fragment of interest can be carried out, for example, by excising a band corresponding to the size of the DNA of interest following agarose gel electrophoresis, and extracting DNA from that gel section. The vector and the extracted DNA are treated with a restriction enzyme, to subsequently integrate the extracted DNA into the vector. The DNA sequence coded by the integrated DNA is identified to obtain the DNA sequences coding for VH and VL of interest.

The human antibody CH and CL of the human chimeric antibody may be any human antibodies CH and CL. Examples include human gamma-1 and gamma-2 CH and human kappa CL. Genes encoding human antibody CH and CL may be chromosomal DNAs or cDNAs. DNAs coding for VH and VL of the nonhuman animal-derived monoclonal antibody obtained by the above-described method may bind, for example, with DNAs coding for human antibody CH and CL, respectively, which may be integrated into an expression vector for an animal cell, thereby preparing a vector expressing the chimeric antibody of the present invention.

Examples of an enhancer and a promoter used for expressing the human chimeric antibody include an enhancer and a promoter of the immunoglobulin gene itself or a non-immunoglobulin enhancer and promoter. Since the expression-regulating mechanism of the immunoglobulin gene is common between a mouse and a human, when a mouse, for example, is used as the nonhuman animal, recombinant DNA may be prepared such that the enhancer sequence of the mouse or the human present between J- and C-genes is contained therein.

The expression vector for an animal cell may be, for example, pSV2-gpt (R. C. Mulligan and P. Berg, Science, 209, 1422, 1980). The genes coding for H-chain and L-chain of the human chimeric antibody of the present invention prepared as described above may be integrated into either the same vector or different vectors.

(2) Humanized Antibody

The humanized antibody of the present invention can be obtained by: constructing DNA coding for a V region in which the amino acid sequence coding for CDRs of VH and VL of the nonhuman animal-derived monoclonal antibody that binds to ADAM-15 and inhibits ADAM-15 activity is transplanted into the framework regions (FR) of the human antibody VH and VL; binding the constructed DNA with the cDNA of the human-derived immunoglobulin constant region, which is integrated into an expression vector; and introducing the vector into an appropriate host cell for expression (see L. Rieohmann et al., Nature, 332, 323, 1988; Kettleborough, C. A. et al., Protein Eng., 4, 773-783, 1991; Clark M., Immunol. Today., 21, 397-402, 2000).

The amino acid sequence of each CDR of the nonhuman animal-derived monoclonal antibody can be obtained by comparing an amino acid sequence predicted from the DNA sequences coding for VH and VL of the nonhuman animal-derived monoclonal antibody obtained by the above-described method with all amino acid sequences of known antibody VH and VL. An amino acid sequence of a known antibody may be acquired, for example, from the amino acid sequences of the antibodies registered with the database such as protein databank or the like.

The human antibody FR is not particularly limited as long as the transplanted antibody exhibits the effect of the present invention, but preferably it is a human antibody FR where the V region of a humanized antibody takes similar conformation to that of the V region of the nonhuman animal-derived monoclonal antibody, or it is a human antibody FR sharing high homology with the amino acid sequence of the nonhuman animal-derived monoclonal antibody FR used. Whether or not the V region of the humanized antibody having FR of the selected human antibody has similar conformation to that of the V region of the nonhuman animal-derived monoclonal antibody can be determined, for example, by predicting the conformation by computer modeling based on the DNA sequence information of the V region containing the selected human antibody FR, and comparing it with the V region conformation of the nonhuman animal-derived monoclonal antibody used. The amino acid sequence of the nonhuman animal-derived monoclonal antibody FR used can be acquired from the information of an amino acid sequence predicted from the DNA sequences coding for VH and VL obtained according to the above-described method and the amino acid sequence of CDR. Furthermore, since the V region of the humanized antibody is a human antibody FR having similar conformation to that of the nonhuman animal-derived monoclonal antibody V region or a human antibody FR sharing high homology with the amino acid sequence of the nonhuman animal-derived monoclonal antibody FR used, mutation can appropriately be introduced into the amino acid sequence of the resulting human antibody FR.

DNA sequence coding for the V region of the humanized antibody used is designed as a DNA sequence corresponding to an amino acid sequence obtained by binding the amino acid sequence of nonhuman animal-derived monoclonal antibody CDR and the amino acid sequence of human antibody FR. DNA coding for the V region of the humanized antibody may be prepared according to a method well known to those skilled in the art based on the designed DNA sequence. For example, it may be obtained by chemically synthesizing a DNA fragment having a length of about 100 bp as synthetic DNA based on the designed DNA and amplifying the DNA fragment by PCR. It may also be obtained by binding the DNA fragment of about 100 bp with an enzyme such as ligase, performing PCR using primers coding for sequences at both terminals of the DNA sequence coding for the designed humanized antibody V region, and extracting DNA fragments having the desired length. The DNA coding for the humanized antibody V region used for PCR may also be obtained by a method known as CDR grafting. The DNA coding for the humanized antibody V region used may also be obtained by integrating DNA coding for CDR into DNA of the human antibody V region by site-directed mutagenesis. Site-directed mutagenesis may be carried out, for example, by using Gene Tailor Site-Directed Mutagenesis System (Invitrogen), Transformer site-directed mutagenesis kit (Clontech), Site-Directed Mutagenesis System (Takara Bio) or the like by following the instruction of the kit.

The human antibody CH and CL of the humanized antibody may be any human antibodies CH and CL. Examples include human gamma-1 and gamma-2 CH and human kappa CL. Genes encoding human antibody CH and CL may be chromosomal DNAs or cDNAs. DNAs coding for V region of the humanized antibody obtained by the above-described method may bind, for example, with DNAs coding for human antibody CH and CL, respectively, which may be integrated into an expression vector for an animal cell, thereby preparing a vector expressing the humanized antibody of the present invention.

Examples of an enhancer and a promoter used for expressing the humanized antibody include an enhancer and a promoter of the immunoglobulin gene itself or a non-immunoglobulin enhancer and promoter. Since the expression-regulating mechanism of the immunoglobulin gene is common between a mouse and a human, when a mouse is used, for example, as the nonhuman animal, a recombinant DNA may be prepared such that the enhancer sequence of the mouse or the human present between J- and C-genes is contained therein.

The expression vector for an animal cell may be, for example, pSV2-gpt (R. C. Mulligan and P. Berg, Science, 209, 1422, 1980). The genes coding for H-chain and L-chain of the humanized antibody of the present invention prepared as described above may be integrated into either the same vector or different vectors.

The nonhuman animal-derived monoclonal antibody used for preparing the above-mentioned human chimeric antibody and humanized antibody is not particularly limited as long as it binds to ADAM-15 and inhibits ADAM-15 activity, but it is preferably a mouse monoclonal antibody.

(3) Human Antibody

A human antibody may be obtained, for example, by employing a human antibody phage library or a human antibody-producing transgenic mouse (Tomizuka et al., Nature Genet., 15, 146-156 (1997)).

A human antibody phage library is a library of phages presenting Fab, scFv or the like of human antibodies as fusion proteins on the surfaces thereof by introducing VH and VL genes from an antibody gene pool having various human B cell-derived sequences into a phage gene. Examples of such human antibody phage libraries include a naive nonimmune library prepared by amplifying VH and VL genes of a normal human antibody by RT-PCR from peripheral blood lymphocytes or the like (Cambridge Antibody Technology; Medical Research Council; Dyax; etc.), a synthetic library prepared by selecting certain functional antibody genes in human B cells, and substituting the antigen-binding domain such as the CDR3 domain and the like of the V gene fragment with oligonucleotides coding for random amino acid sequences with appropriate lengths (BioInvent; Crucell; Morphosys), and an immune library prepared from lymphocytes from patients suffering from cancer, an autoimmune disorder or an infectious disease or person vaccinated with the target antigen.

For example, a naive human antibody phage library may be prepared by the following method. mRNA is prepared from human peripheral blood. V gene cDNA is synthesized with primers specific to constant regions of immunoglobulin gamma-, mu-, kappa- and lambda-chains to synthesize each V gene by using a DNA primer set specific to V gene family, which are linked by PCR using linker DNA coding for a linker peptide such as $(Gly4Ser)_3$, thereby synthesizing scFv gene. Restriction-enzyme sites for vector introduction are attached at both ends of the synthesized scFv gene, which is then inserted into a phagemid vector such as pCANTAb5E. *E. coli* is transformed with this vector, and rescue is performed with a helper phage.

When a human antibody phage library is used, for example, ADAM-15 as a target is immobilized onto a solid phase and reacted with a phage antibody library. After washing the unbound phages away, the bound phages are collected, thereby obtaining the desired clones (panning). Furthermore, the obtained phages are amplified to repeat panning against the amplified library so as to refine the obtained clones. By analyzing the VH and VL genes of the obtained clones, a complete human antibody having these gene sequences may be made.

A human antibody-producing transgenic mouse is a mouse obtained by introducing human antibody Ig gene into an endogenous immunoglobulin (Ig) gene-knockout mouse. A human antibody-producing transgenic mouse can be obtained, for example, by the following method. Human-mouse hybrid cells are treated with colcemid (spindle formation inhibitor) for 48 hours to form microcells, structures each having one or more chromosomes surrounded by a nuclear membrane. The microcells isolated in the presence of cytochalasin B are fused with chromosomal recipient cells (mouse ES cells) with polyethylene glycol to form microcell hybrid ES cells, which are transferred into mouse embryos.

The human antibody-producing transgenic mouse as an immunized animal can be immunized with the antigen according to the above-described anti-ADAM-15 antibody preparation method, thereby obtaining an anti-ADAM-15 human antibody.

3. Preparation of Antibody Fragment

The antibody fragments of the present invention ($F(ab')_2$, Fab', Fab, scFv, dsFv, a polymer thereof, a diabody or a peptide containing CDR) can be prepared according to the following method.

The $F(ab')_2$ fragment of the present invention can be obtained by treating the ADAM-15-binding IgG antibody of the present invention with a proteolysis enzyme pepsin to cleave at the 234th amino acid residue of the H-chain to give an antibody fragment with a molecular weight of about 100,000 having antigen-binding activity. The $F(ab')_2$ fragment of the present invention can also be obtained through thioether binding or disulfide binding of Fab' described below.

The Fab' fragment of the present invention can be obtained by treating ADAM-15-binding $F(ab')_2$ of the present invention obtained by the above-described method with a reducing agent dithiothreitol. In addition, the Fab' fragment of the present invention can be obtained by inserting DNA coding for ADAM-15-binding antibody Fab' of the present invention into an expression vector, and introducing the vector into a host cell for expression.

The Fab fragment of the present invention can be obtained by treating the ADAM-15-binding antibody of the present invention with a proteolysis enzyme papain to cleave at the 224th amino acid residue of the H-chain to give an antibody fragment with a molecular weight of about 50,000 having antigen-binding activity where about half of the region at the N-terminal side of the H-chain and the entire region of the L-chain are bound to each other via disulfide binding. In addition, the Fab fragment of the present invention can be obtained by inserting DNA coding for the ADAM-15-binding antibody Fab of the present invention into an expression vector, and introducing the vector into a host cell for expression.

The scFv of the present invention can be obtained by acquiring cDNAs coding for VH and VL of the ADAM-15-binding antibody of the present invention, and inserting DNA coding for a linker sequence therebetween to construct DNA coding for scFv. Then, this DNA is inserted into an expression vector, which is then introduced into a host cell for expression. The length of the linker is not particularly limited as long as it allows association between VH and VL, but it is preferably 10 to 20 residues, and more preferably 15 residues. In addition, the sequence of the linker is not particularly limited as long as it does not interfere with the folding of the polypeptide chains of two domains VH and VL, but it is preferably a linker consisting of glycine and/or serine, and more preferably GGGGS (G: glycine, S: serine) or a repetitive sequence thereof.

The dsFv of the present invention can be obtained by substituting one amino acid residue in each of VH and VL with a cysteine residue by site-directed mutagenesis, and linking VH and VL via disulfide binding between the cysteine residues. The amino acids to be substituted are not particularly limited as long as they have no effect on the antigen binding in terms of conformation.

The diabody of the present invention can be obtained by constructing the amino acid sequence of the linker in the above-described DNA coding for scFv to be 8 residues or less (preferably 5 residues), inserting the DNA into an expression vector, and introducing the vector into a host cell for expression. The bispecific diabody can be obtained by preparing a scFv by combining DNAs of VH and VL from two different scFvs.

The CDR-containing peptide of the present invention can be obtained by constructing DNA coding for the amino acid sequence of CDR of ADAM-15-binding antibody VH or VL of the present invention, inserting the DNA into an expression vector, and introducing the vector into a host cell for expression.

4. Selection of Antibody that Recognizes ADAM-15 Disintegrin Domain but not RGD Sequence in ADAM-15 Disintegrin Domain An antibody or the like that binds to ADAM-15 of the present invention can be obtained by selecting an antibody or the like that recognizes the intended epitope among the antibodies or the like obtained by the above-described method. An antibody that binds to ADAM-15 of the present invention can also be obtained by administering a peptide having the intended epitope sequence (preferably, disintegrin domain sequence) as an antigen in the above-described method for preparing the anti-ADAM-15 antibody.

An antibody or the like that recognizes the ADAM-15 disintegrin domain can be obtained by a selection method well known to those skilled in the art. For example, an antibody or the like that recognizes the ADAM-15 disintegrin domain can be obtained by determining the binding activity between the ADAM-15 disintegrin domain peptide and the antibodies or the like obtained by the above-described method, and selecting an antibody or the like with high binding activity. The association constant ($K_a$) between the anti-ADAM-15 antibody or the like of the present invention and the ADAM-15 disintegrin domain is, for example, at least $10^7 M^{-1}$, preferably at least $10^8 M^{-1}$, and more preferably at least $10^9 M^{-1}$. Such an association constant is still more preferably $10^{10} M^{-1}$, $10^{11} M^{-1}$, $10^{12} M^{-1}$ or higher, for example, $10^{13} M^{-1}$ or higher. Alternatively, an antibody or the like that recognizes the ADAM-15 disintegrin domain can be obtained by: preparing a full-length ADAM-15 mutant or an ADAM-15 mutant fragment by introducing alanine mutation into the ADAM-15 disintegrin domain among the ADAM-15 amino acids; determining the binding activities between this mutant or the like and the antibodies or the like obtained by the method above; comparing the binding activities with those between the antibodies or the like and full-length ADAM-15 or an ADAM-15 fragment; and selecting an antibody or the like having lower binding activity with the mutant.

An antibody or the like that recognizes the ADAM-15 disintegrin domain but not the RGD sequence in the ADAM-15 disintegrin domain can be obtained by selecting an antibody that does not recognize the RGD sequence in the ADAM-15 disintegrin domain from the antibodies or the like that recognize the ADAM-15 disintegrin domain obtained by the above method by a method well known to those skilled in the art. For example, an antibody or the like that recognizes the ADAM-15 disintegrin domain but not the RGD sequence in the ADAM-15 disintegrin domain can be obtained by: preparing a full-length ADAM-15 mutant or an ADAM-15 mutant fragment by introducing alanine mutation into at least one amino acid of the RGD sequence in the ADAM-15 disintegrin domain among the ADAM-15 amino acids; determining the binding activities between this mutant or the like and the obtained antibodies or the like; comparing the binding activities with those with full-length ADAM-15 or an ADAM-15 fragment; and selecting an antibody or the like having no difference between the binding activities.

5. Selection of Antibody that Recognizes ADAM-15 Disintegrin Domain but not Loop Region in ADAM-15 Disintegrin Domain An antibody or the like that recognizes the ADAM-15 disintegrin domain but not the loop region in the ADAM-15 disintegrin domain can be obtained by selecting an antibody or the like that does not recognize the loop region in the ADAM-15 disintegrin domain from the antibodies or the like that recognize the ADAM-15 disintegrin domain obtained by the method above by a method well known to those skilled in the art. For example, an antibody or the like that recognizes the ADAM-15 disintegrin domain but not the loop region in the ADAM-15 disintegrin domain can be obtained by: preparing a full-length ADAM-15 mutant or an ADAM-15 mutant fragment by introducing alanine mutation into at least one amino acid of the loop region in the ADAM-15 disintegrin domain among the ADAM-15 amino acids; determining the binding activities between this mutant or the like and the obtained antibodies or the like; comparing the binding activities with those with full-length ADAM-15 or an ADAM-15 fragment; and selecting an antibody or the like having no difference between the binding activities.

The binding between the obtained antibodies and ADAM-15, a fragment thereof or a mutant thereof can be measured by a method well known to those skilled in the art. Examples of such a method include Western blotting, X-ray crystallographic analysis as well as Biacore system (Biacore).

6. Determination of Inhibitory Activity for ADAM-15 and Integrin $\alpha v\beta 3$-Dependent Cell Adhesion Whether or not the obtained antibody inhibits ADAM-15 and integrin $\alpha v\beta 3$-dependent cell adhesion can be examined, for example, by comparing the binding of integrin $\alpha v\beta 3$-expressing cell to a plate having ADAM-15 recombinant protein immobilized thereon in the presence/absence of the obtained antibody. Whether or not the determined cell adhesion is integrin $\alpha v\beta 3$-dependent cell adhesion can be determined by determining binding of integrin $\alpha v\beta 3$-expressing cell to a plate having ADAM-15 recombinant protein immobilized thereon in the presence/absence of an anti-integrin $\alpha v\beta 3$ antibody as a control.

7. ADAM-15 and Integrin $\alpha 9\beta 1$-Dependent Cell Adhesion

Whether or not the obtained antibody inhibits ADAM-15 and integrin $\alpha v\beta 3$-dependent cell adhesion can be examined, for example, by comparing the binding of integrin $\alpha 9\beta 1$-expressing cell to a plate having ADAM-15 recombinant protein immobilized thereon in the presence/absence of the obtained antibody. Whether or not the determined cell adhesion is integrin $\alpha 9\beta 1$-dependent cell adhesion can be determined by determining binding of integrin $\alpha 9\beta 1$-expressing cell to a plate having ADAM-15 recombinant protein immobilized thereon in the presence/absence of an anti-integrin $\alpha 9\beta 1$ antibody as a control.

5. Pharmaceutical Composition

Since the resulting antibody of the like is capable of intercepting intracellular signaling of information by inhibiting binding between ADAM-15 and integrin, it can be used as a therapeutic drug for diseases associated with such a signal. Diseases targeted by an antibody of the like of the present invention can be found by observing binding inhibition in the presence of the obtained antibody in vitro or in vivo by using cells expressing ADAM-15 and integrin or cancer cells.

A formulation using an antibody (in particular, monoclonal antibody) or the like of the present invention as an active element may be used as a therapeutic agent or a prophylactic agent for cancers (esophagus cancer, thyroid cancer, bladder cancer, colorectal cancer, gastric cancer, pancreatic cancer, thoractic cancer, liver cancer, lung cancer, breast cancer, neuroblastoma, glioblastoma, uterus cancer, ovary cancer, prostate cancer, Wilms' tumor) and metastases thereof, diseases caused by cell proliferation or angiogenesis such as endometriosis; arthritis, infectious diseases (hepatitis, etc.), bronchial asthma, fibrosis, autoimmune disorders (for example, systemic lupus erythematosus (SLE), polymyositis (PM), autoimmune thyroid disease, tubulointerstitial nephritis, myasthenia gravis (EAMG), organ-specific autoimmune disorder, etc.), rheumatic arthritides (chronic rheumatoid arthritis (RA), osteoarthritis (OA)), multiple sclerosis (relapsing-remitting multiple sclerosis, etc.), inflammatory enterocolitis (ulcerative colitis, Crohn's disease, etc.), progressive systemic sclerosis (PSS), Sjogren's syndrome, dermatomyositis (DM), periarteritis nodosa (PN), thyroid diseases (Grave's disease, etc.), Guillain-Barre syndrome, primary biliary cirrhosis (PBC), idiopathic thrombocytopenic purpura, autoimmune hemolytic anemia, amyotrophic lateral sclerosis (ALS), type I diabetes, transplant rejection, adhesions after operation, endometriosis, psoriasis, lupus, allergy, asthma, diseases caused by inflammatory diseases or cell migration such as abnormal neutrophil function; occlusive vascular diseases such as restenosis after revascularization, heart coronary occlusive vascular disease, brain occlusive vascular disease, kidney occlusive vascular disease, peripheral occlusive vascular disease, arteriosclerosis and cerebral infarction, diseases caused by intimal hypertrophy, or the like.

The antibody or the like obtained by the above-described method is purified if necessary, and subsequently made into a formulation according to a routine method to be used as a prophylactic and/or therapeutic agent for various diseases and the like. Where the antibody of the present invention is used as a medicine, examples of administration site include oral administration, intraoral administration, intratracheal administration, subcutaneous administration, intramuscular administration and intravascular (intravenous) administration. The antibody of the present invention may be administered alone or as a pharmaceutical composition using a pharmaceutically and pharmacologically acceptable carrier (see "Japanese Pharmaceutical Excipients" Yakuji Nippo, and "Handbook of Pharmaceutical Excipients" APhA Publications), a diluent, an additive or the like. The pharmaceutical composition of the present invention may also be provided as a preparation suitable for parenteral or oral administration.

Examples of compositions for parenteral administration include an injectable agent, nasal drops, a suppository, a patch and an ointment. Injectable agents comprise preparations such as an intravenous injectable agent, a subcutaneous injectable agent, an intradermal injectable agent, an intramuscular injectable agent and a drip injectable agent. Such injectable agents may be prepared according to a known method, for example, by dissolving, suspending or emulsifying the antibody or the like in a sterile aqueous or oily fluid generally used for injectable agents. An aqueous fluid for injection may be, for example, an isotonic solution including physiological saline, glucose, sucrose, mannitol, other adjuvants and the like, which may be used in combination with an appropriate solubilizing aid such as alcohol (e.g., ethanol), polyalcohol (e.g., propylene glycol, polyethylene glycol), nonionic surfactant (e.g., polysorbate 80, polysorbate 20, HCO-50 (polyoxyethylene (50 mol) adduct of hydrogenated castor oil)) or the like. An oily fluid may be, for example, sesame oil, soybean oil or the like, which can be used in combination with a solubilizing aid such as benzyl benzoate, benzyl alcohol or the like. The prepared injection solution is usually charged in an appropriate ampule, vial or syringe. A suppository used for rectal administration may be prepared by mixing the antibody with a base generally used for nasal drops or a suppository. Alternatively, an appropriate excipient can be added to the antibody to prepare a lyophilized formulation, which can be used as an injection solution by dissolving it with an injectable water or physiological saline upon use. Generally, oral administration of a protein such as an antibody is known to be difficult because it is degraded by the digestive organs, but inventive approaches on the antibody fragment, the modified antibody fragment and the preparations leave open the possibility of oral administration. Examples of formulations for oral administration include a capsule, a tablet, syrup and granule.

The above-described parenteral pharmaceutical composition is preferably prepared into a unit-dose preparation that is suitable for the dosage of the active element. Examples of such a unit-dose preparation include injectable agents (ampule, vial, prefilled syringe), nasal drops and suppository, where each of which contains the above-described antibody for generally 5 to 500 mg per unit-dose preparation, and preferably 5 to 100 mg for an injectable agent and 10 to 250 mg for other preparations.

The dosage of the pharmaceutical composition of the present invention can appropriately be selected according to the subject of administration, targeted disease, condition, administration route and the like. For example, when the antibody of the present invention is used for prophylaxis and/or treatment of a cancer patient, it is conveniently administered by intravenous injection usually at about 0.01 to 20 mg/kg weight, preferably about 0.1 to 10 mg/kg weight and more preferably about 0.1 to 5 mg/kg weight per dose for about 1 to 10 times a month and preferably for about 1 to 5 times a month. In the case of other parenteral and oral administrations, a dosage similar to the above dosage may apply. When the condition is particularly severe, the dosage or the number of administration may be increased according to the condition.

6. Diagnostic Drug

Since the antibody or the like of the present invention can specifically recognize ADAM-15, it can be used for quantitation of ADAM-15 in a test solution. A diagnostic drug comprising the antibody or the like of the present invention may be used as a diagnostic agent for an inflammatory disease such as rheumatoid arthritis, hepatitis, bronchial asthma, fibrosis, diabetes, cancer metastasis, arteriosclerosis, multiple sclerosis, granuloma or the like, and as a diagnostic agent for chronic antirejection after organ transplantation or an autoimmune disorder such as systemic autoimmune disorder, erythematodes, uveitis, Behcet's disease, polymyositis, proliferative glomerulonephritis, sarcoidosis or the like. A diagnostic drug of the present invention may be based on a known method employing an antibody molecule. Examples of such methods include ELISA (Catty, Raykundalia, 1989), radioimmunoassay (Catty, Murphy, 1989), immunohistochemical method (Heider et al., 1993), immunometric assay and Western blot. A specimen of a diagnostic drug of the present invention may be, for example, a tissue sample or fluid collected from a test subject as a biopsy specimen. The biopsy specimen used is not particularly limited as long as it can be a subject of immunoassay for ADAM-15, and examples include tissue, blood, urine, serous fluid, spinal fluid, joint fluid, aqueous humour, tear fluid, saliva and a fraction or a processed material thereof. Analysis with the diagnostic drug of the present invention may be carried out qualitatively, quantitatively or semiquantitatively.

In order to use the obtained antibody as a diagnostic drug, for example, various labels (for example, biotin label, FITC label, APC label) can be performed by employing a known method or a commercially available kit. Preferably, such a label is biotin label using Biotin Labeling Kit (Dojindo Laboratories).

There is no special condition or setting of manipulation or the like required for applying these immunoassays to the measurement of the present invention. A measurement system can be established by employing conditions and manipulation that are generally used for each method with usual technical consideration by those skilled in the art. For details of these general technical means, reference can be made to reviews, textbooks and the like.

Thus, by using an antibody or the like of the present invention, ADAM-15 can be quantitated in a highly sensitive manner. In addition, by employing an ADAM-15 quantitation method in vivo using the antibody or the like of the present invention, prediction, presence or absence, degree and prognosis of various ADAM-15-associated diseases, and effect of medicines or the like therefor can be diagnosed. For example, when an increase or a decrease of ADAM-15 concentration is detected, it may be diagnosed that there is a high possibility of ADAM-15-associated disease such as an inflammatory disease or a high possibility of suffering the disease in the future.

Besides, an antibody or the like of the present invention may be used for preparing an antibody column used for purifying ADAM-15, detection of ADAM-15 contained in individual fraction upon purification, analysis of ADAM-15 behavior in the test cell or the like.

Hereinafter, the present invention will be described in more detail by means of examples although the present invention should not be limited thereto.

Unless otherwise stated in the following examples, the following media were used for cell culture. For culturing CHO-K1 cell, 5% FCS-containing D-MEM Ham's F-12 medium (Wako); for culturing CHO cell constitutively expressing human α9 integrin (hα9/CHO), 600 µg/ml G418, 5% FCS-containing D-MEM Ham's F-12 medium; for culturing human kidney cancer cell line (NRC-12) and human breast cancer cell line (MDA-MB-435S: 435S), 10% FCS-containing TIL medium (IBL); and for culturing COS-7 cell, 10% FCS-containing D-MEM (Wako) medium.

EXAMPLES

Example 1

Preparation of Cell Line Constitutively Expressing Human α9 Integrin

Human α9 integrin gene was cloned from total RNA extracted from G361 cell by performing PCR using cDNA synthesized with ReverTraAce (TOYOBO) as a template. Cloning of human α9 integrin gene was carried out in two fragments, i.e., 5' and 3' fragments, with the following primers.

Human α9 integrin gene 5' fragment:

```
                                      (SEQ ID NO: 1)
Sense primer: 5'-TTTTAAGCTTGCCACCATGGGCGGCCCGGCTG-
3'
                                      (SEQ ID NO: 2)
Anti-sense primer: 5'-AAACTGCAGTCCGGAGCACTGGATTTAT
CTTCT-3'
```

Human α9 integrin gene 3' fragment:

```
                                      (SEQ ID NO: 3)
Sense primer: 5'-AAATCCGGATGTTTGGTCCATATC-3'

(SEQ ID NO: 4)
Anti-sense primer: 5'-AAATCTAGATCACTGGTTTTTCTGGACC
CAGTC-3'
```

The PCR product of the human α9 integrin gene 5' fragment was treated with restriction enzymes HindIII and PstI while the PCR product of the 3' fragment was treated with a restriction enzyme EcoRV at 37° C. for an hour, which were respectively integrated into pBluescript SK(+) vectors (Stratagene) for plasmid extraction (5' fragment: α9F/pBS, 3' fragment: α9R/pBS). Each of the plasmids was treated with restriction enzymes AccIII and XbaI at 37° C. for an hour. The α9R fragment was purified and inserted into AccIII/XbaI site of α9F/pBS. This plasmid was treated with restriction enzymes HindIII and XbaI to excise the insert site, which was inserted into pcDNA3.1(+) vector (Invitrogen) (α9/pcDNA3.1(+)).

α9/pcDNA3.1(+) was transfected into CHO-K1 cell with Lipofectamine-2000 (Invitrogen), and drug-resistant cells were screened with DMEM Ham's F-12 (WAKO) containing 10% FCS (SIGMA-Aedrich) in which Geneticin G418 (Invitrogen) was adjusted to be 600 µg/ml. The screened cells were subjected to repeated steps of screening by flow cytometry and limiting dilution to establish a CHO-K1 cell constitutively expressing human α9 integrin (hereinafter, referred to as a "hα9/CHO cell").

Example 2

Preparation of Human ADAM-15 Disintegrin Domain/pGEX-6P-1

DNA strand of human ADAM-15 disintegrin domain was replicated by PCR method. 1 µL of HUVEC cDNA was used as a template, and 0.5 µL each of 100 µM sense primer and 100 µM anti-sense primer, 8 µL of 2.5 mM dNTP mix, 0.5 µL of EX-Tag polymerase (2.5 U/100 µL: Takara) and 10 µL of 10×PCR buffer were added to 79.5 µL of ultrapure water to prepare a PCR reaction solution. Using a thermal cycler, PCR reaction was performed with: a cycle of 94° C. for 5 minutes; 35 cycles of 94° C. for a minute, 55° C. for a minute and 72° C. for a minute; and a cycle of 72° C. for 5 minutes. The primers used were as follows.

```
                                      (SEQ ID NO: 5)
Sense primer: 5'-CCTATGGCTGCTTTCTGC-3'

(SEQ ID NO: 6)
Anti-sense primer: 5'-CATGCACACAGCTTGCCC-3'
```

The PCR product was subjected to electrophoresis with 2% agarose gel, and the band of interest was excised and purified with DNA purification kit (Wizard SV Geland PCR Clean-up System: PROMEGA). The prepared DNA strand was replicated by TA cloning. The TA cloning procedure was as follows. 1 µL of the PCR product, 0.5 µL of pCRII-TOPO vector (Invitrogen) and 1 µL of salt solution (Invitrogen) were added to 3.5 µL of sterilized water to prepare a reaction solution, which was left to stand at room temperature for 5 minutes and then used for transformation of JM-109. Using the thus-prepared human ADAM-15 disintegrin domain/TOPO as a template, BamHI/XhoI site was added to the DNA strand of human ADAM-15 disintegrin domain. 0.5 µL of the template DNA, 0.2 µL each of 100 µM sense primer and 100 µM anti-sense primer, 8 µL of 2.5 mM dNTP mix, 0.5 µL of EX-Tag polymerase (2.5 U/100 µL: Takara) and 10 µL of 10×PCR buffer were added to 80.6 µL of ultrapure water to prepare a PCR reaction solution. Using a thermal cycler, PCR reaction was performed with a cycle of 94° C. for 5 minutes; 35 cycles of 94° C. for a minute, 53° C. for a minute and 72° C. for 30 seconds; and a cycle of 72° C. for 5 minutes. The primers used were as follows.

Sense primer: 5'-AAGGATCCGCTGCTTTCTGCGGA-3' (SEQ ID NO: 7)

Anti-sense primer: 5'-ATTCTCGAGATCCCCTAGGCTGACAT-3' (SEQ ID NO: 8)

The PCR product was subjected to electrophoresis with 2% agarose gel, and the band of interest was excised and purified with DNA purification kit (Wizard SV Geland PCR Clean-up System:PROMEGA). The prepared DNA strand was inserted into pGEX-6P-1 vector treated with BamHI/XhoI restriction enzymes. This was used for transformation of JM-109 and replicated. Subsequently, the resultant was purified with midi prep kit (QIAGEN).

Example 3

Preparation of Human ADAM-15 Disintegrin Domain-GST Protein

The human ADAM-15 disintegrin domain/pGEX-6P-1 prepared in Example 2 was used for transformation of JM-109, amplified in an LB medium added with ampicillin (SIGMA-Ardrich), and added with 200 µM IPTG (Amersham Bioscience) in the logarithmic growing phase to induce GST fusion protein expression. E. coli was collected and then suspended in a NETN-150 buffer (50 mM Tris (pH 7.2), 1 mM EDTA, 150 mM NaCl, 0.5% NP-40) and subjected to sonication to extract the protein. Following centrifugation, the supernatant was added to glutathione sepharose beads 4B (Amersham Bioscience) and mixed by inverting at 4° C. for 2 hours. The beads were washed with an NETN-100 buffer (50 mM Tris (pH 7.2), 1 mM EDTA, 100 mM NaCl, 0.5% NP-40), and eluted with a reduced glutathione solution (100 mM Tris (pH 8.8), 20 mM Reduced Glutathione (Wako)) to be used as GST fusion protein. In order to prepare a GST-cleaved protein, the same procedure was applied until adsorption of the E. coli-expressed protein to glutathione sepharose beads. After washing the beads with an NETN-100 buffer, enzyme treatment was performed with prescission protease (Amersham Bioscience) to cleave GST.

Example 4

Preparation of Human ADAM-15 Disintegrin Domain Protein (RAA Substitute)

A protein having the RGD sequence in the human ADAM-15 disintegrin domain protein substituted with RAA sequence (hereinafter, referred to as "human ADAM-15 disintegrin domain protein (RAA substitute)") was prepared by the following method. While using the human ADAM-15 disintegrin domain/pGEX-6P-1 prepared in Example 2 as a template, 1.25 µL each of 100 µg/ml sense primer and 100 µg/ml anti-sense primer, 1 µL of 2.5 mM dNTP mix, 1 µL of pfu turbo polymerase (2.5 U/µL) and 5 µL of a 10×PCR buffer were added to 40.4 µL of ultrapure water to prepare a PCR reaction solution. Using a thermal cycler, PCR reaction was performed with a cycle of 95° C. for 30 seconds; 18 cycles of 95° C. for 30 seconds, 55° C. for a minute and 68° C. for 5 and a half minutes; and a cycle of 72° C. for 7 minutes. The primers used were as follows.

Sense primer: 5'-CAGTGTCCTACCAGAGCTGCTTGTGACTTGCCTG-3' (SEQ ID NO: 9)

Anti-sense primer: 5'-CAGGCAAGTCACAAGCAGCTCTGGTAGGACGACACTG-3 (SEQ ID NO: 10)

Afterward, the resultant was treated with a restriction enzyme DpnI according to the manual of QuickChange Site-Directed Mutagenesis Kit (Invitrogen), and inserted into a pGEX-6P-1 vector. This vector was used for transformation of JM-109 and replicated. Subsequently, purification was performed using midi prep kit (QIAGEN). Then, a GST fusion protein was prepared by the same method as in Example 3, and GST-removed human ADAM-15 disintegrin domain protein (RAA substitute) was prepared by treating GST with prescission protease.

Example 5

Preparation of Anti-Human ADAM-15 Disintegrin Domain Monoclonal Antibody (8F7)

The human ADAM-15 disintegrin domain-GST protein prepared in Example 3 was used to immunize a BALB/c mouse (female, 7-week-old: SAMKYO LABO SERVICE CORPORATION) for a total of 4 times. The mouse was immunized by using an emulsion of 100 µg of the protein in a complete Freund's adjuvant (SIGMA) and an emulsion of 50 µg of the protein in an incomplete Freund's adjuvant (SIGMA) for primary immunization and the subsequent immunizations, respectively. After four times of immunizations, blood was drawn from the mouse, and the serum was used to determine the antibody titer by ELISA. Thereafter, 50 µg of the protein was dissolved in PBS and used for booster.

Following immunization, spleen was removed from the mouse. The spleen cell and X63-Ag8-653 myeloma cell were fused using polyethylene glycol (IBL), and then subjected to selection culture in a HAT medium. Once formation of hybridoma colony was confirmed, the culture supernatant was used to screen the ability of binding to the antigen protein by ELISA method. According to ELISA method, 50 ng of human ADAM-15 disintegrin domain-GST protein as the antigen was immobilized onto each well as a solid phase, while a 2-fold dilution of the hybridoma culture supernatant was used as the primary antibody. Positive colonies were subjected to limiting dilution twice to obtain a single type of clone. The culture supernatant of the resulting clone was purified with an antigen column to establish a monoclonal antibody (clone name: 8F7, hereinafter referred to as "8F7"). The hybridoma cell producing this monoclonal antibody was deposited with the International Patent Organism Depositary (IPOD), the National Institute of Advanced Industrial Science and Technology (AIST), Tsukuba Central 6, 1-1-1, Higashi, Tsukuba, Ibaraki-ken (zip code: 305-8566) on Feb. 13, 2008 as Receipt No. FERM ABP-10950 (Accession No. FERM BP-10950).

The antigen specificity of the prepared 8F7 was confirmed by ELISA method. According to ELISA method, GST, human ADAM-15 disintegrin domain-GST protein, human ADAM-15 disintegrin domain loop region-GST protein, human ADAM-15 disintegrin domain protein, human ADAM-15 disintegrin domain protein (RAA substitute) and mouse osteopontin N-half-GST protein were each immobilized onto a solid phase in serial dilutions from 10 µg/ml, and 8F7 adjusted to 0.1 µg/ml was used as the primary antibody. The results are shown in FIG. 1. According to the examination by ELISA method, although cross-reaction with GST was present, the reaction was very weak. On the other hand, reaction against human ADAM-15 disintegrin domain-GST was found to be strong. Furthermore, binding was not found with the loop region in the disintegrin domain that was said to be necessary for adhesion to integrin (hereinafter, referred to as "loop region").

Moreover, antigen specificity of the prepared 8F7 was confirmed by Western blot. Human ADAM-15/pOTB7 (purchased from Invitrogen) was subjected to restriction enzyme treatment with XhoI and BamHI and inserted into pcDNA 3.1(+) vector (Invitrogen) similarly treated with the restriction enzymes. This was used for transformation of JM-109 and replicated. Then, midi prep kit (QIAGEN) was used for purification, thereby obtaining human ADAM-15/pcDNA 3.1(+). COS-7 cell was cultured to 80% confluency in a 6 cm culture plate and cultured using 3 ml of OPTI-MEM medium (GIBCO) added with 4 μg of human ADAM-15/pcDNA 3.1 (+) and 20 μL of Lipofectamine-2000 (Invitrogen) at 37° C. for 6 hours. Then, the medium was exchanged for 3 ml of 10% FCS-containing DMEM medium, and culture was performed at 37° C. for 48 hours to obtain human ADAM-15-transfected COS-7 cell.

COS-7 cell transiently overexpressing the prepared ADAM-15 and untransfected COS-7 cell were dissolved in protease inhibitor (complete mini: Roche)-containing LIPA buffer. The cell lysates were subjected to electrophoresis with 10% SDS, and transferred onto PVDF membranes (MILLIPORE). The transferred PVDF membranes were blocked with 5% skimmed milk/TBS-T at room temperature for an hour, then washed with TBS-T for 3 times, added with 8F7 (0.5 μg/ml) prepared in Example 5 and allowed to react at 4° C. overnight. After washing with TBS-T for 3 times, 10000-fold diluted secondary antibody (anti-mouse IgG, HRP-labeled: Jackson immunoresearch) was added for reaction at room temperature for an hour. After washing with TBS-T for 3 times, the resultant was allowed to react with ECL solution (GE imaginationatwork) at room temperature for 5 minutes, and transferred onto a film in a darkroom for development.

The results are shown in FIG. 2. According to the examination by Western blot, band was detected only for the cell lysate of COS-7 transiently overexpressing human ADAM-15, showing that 8F7 specifically recognized human ADAM-15.

Example 6

Comparison of Binding Activities of Anti-ADAM-15 Monoclonal Antibodies 23G9 and 8F7

Binding activity of a commercially available anti-ADAM-15 monoclonal antibody 23G9 (R & D) was compared to that of 8F7 according to the same method as the ELISA method described above.

The results are shown in FIG. 3. 8F7 showed high RGD sequence-independent binding activity to the ADAM-15 disintegrin domain. On the other hand, binding activities of 23G9 to human ADAM-15 disintegrin domain (d.d.) and human ADAM-15 disintegrin domain-GST protein (d.d.-GST) were lower than that to GST, showing that 23G9 does not recognize the ADAM-15 disintegrin domain. Hence, 8F7 was suggested to have various functions that were previously unknown and owe to ADAM-15 inhibition by binding to a binding site different from those of previously known anti-ADAM-15 antibodies.

Example 7

Cell Adhesion and Cell Adhesion Inhibitory Test Using hα9/CHO Cell

GST-removed human ADAM-15 disintegrin domain recombinant protein or human ADAM-15 disintegrin domain protein (RAA substitute) was prepared to be 0 to 5 μg/mL in PBS, added at 50 μL to each well of a 96-well plate, incubated at 37° C. for an hour, and immobilized. Thereafter, 200 μL each of 0.5% BSA/PBS was added to each well and incubated at room temperature for an hour for blocking reaction. After washing with PBS, hα9/CHO cell prepared in Example 1 or untransfected CHO-K1 cell was prepared to be $1 \times 10^5$ cells/ml in 0.25% BSA-containing medium (D-MEM Ham's F-12), which was added at 200 μL each to each well and incubated at 37° C. for an hour to allow adhesion to the protein immobilized on the solid phase. Subsequently, washing was performed with PBS that had already been warmed to 37° C. to remove cells that did not adhere. 50 μL each of crystal violet was added to each well and incubated at room temperature for 30 minutes to immobilize and stain the cells. After washing with tap water, 100 μL each of 20% acetic acid in water was added to each well to dissolve the cells, and then absorbance at 590 nm was determined with a plate reader.

In the same manner as the cell adhesion test, GST-removed human ADAM-15 disintegrin domain recombinant protein (prepared to be 2.5 μg/ml) was immobilized and subjected to blocking reaction. In the cell adhesion inhibitory activity test for ADAM-15 inhibition, 8F7 in serial dilutions of 0-10 μg/ml was added to the solid phase protein, incubated at 37° C. for 20 minutes to allow adhesion of the cells. Thereafter, cell adhesion was examined in the same manner as the cell adhesion test.

The results from the adhesion test of ha9/CHO cell and untransfected CHO-K1 cell (control) to human ADAM-15 disintegrin domain (hereinafter, referred to as "d.d.") and human ADAM-15 disintegrin domain (RAA substitute) (hereinafter, referred to as "d.d.-RAA") are shown in FIG. 4A. The cell adhesion activity of hα9/CHO cell to solid phase d.d. became higher in a solid phase concentration-dependent manner. Moreover, since the cell adhesion activity of hα9/CHO cell to solid phase d.d.-RAA was almost equivalent to that to solid phase d.d., showing that interaction between the hα9/CHO cell and d.d. was independent from the RGD sequence in d.d. Here, the CHO-K1 cell is endogenously expressing integrins that bind to the RGD sequence, for example, αvβ1 integrin, αvβ5 integrin, α5β1 integrin or the like (Eto, K., Huet, C., Tarui, T., Kupriyanov, S., Liu, H. Z., Puzon-McLaughlin, W., Zhang, X. P., Sheppard, D., Engvall, E., and Takada, Y. Functional classification of ADAMs based on a conserved motif for binding to integrin alpha 9beta 1: implications for sperm-egg binding and other cell interactions. J Biol Chem, 277: 17804-17810, 2002.). Thus, whether or not the cell adhesion of the CHO-K1 cell to solid phase d.d. or d.d.-RAA surface owed to these integrins was examined As a result, the untransfected CHO-K1 cell showed low cell adhesion activity regardless of the presence of solid phase d.d. and d.d.-RAA. Hence, adhesion of hα9/CHO to the solid phase ADAM-15 disintegrin domain surface appears to be adhesion mediated by α9 integrin. In addition, since the adhesion of hα9/CHO to the solid phase ADAM-15 disintegrin domain surface did not weaken for d.d.-RAA, adhesion between α9 integrin and ADAM-15 disintegrin domain is considered to be independent from the RGD sequence in the ADAM-15 disintegrin domain.

The results from the test of 8F7 antibody to inhibit adhesion of hα9/CHO cell to solid phase d.d. and d.d.-RAA surface are shown in FIG. 4B. 8F7 antibody inhibited cell adhesion of hα9/CHO to d.d. and d.d.-RAA in a concentration-dependent manner. Since the adhesion of hα9/CHO cell to solid phase d.d. and d.d.-RAA surfaces seem to be adhesion via α9 integrin considering the above results, 8F7 was confirmed to suppress interaction between human ADAM-15 and human α9β1 integrin.

Example 8

Expression of Integrin in Human Kidney Cancer Cell Line NRC-12

In order to examine RGD-independent adhesion suppression by 8F7 by using human kidney cancer cell line NRC-12 cell, integrin expression in NRC-12 cell was confirmed by flow cytometry. The cells were prepared to be $5\times10^6$/ml in 0.5% BSA/0.01 $NaN_3$/PBS (FACS buffer), and 100 ml each of which was added to each well of a 96-well V-bottom plate. The cells were collected with a plate centrifuge. Subsequently, 100 ml each of CFBS was added to each well and incubated on ice for 30 minutes to block the Fc receptor on the cell membrane surface. 0.5 µg of the primary antibody was added and incubated on ice for 20 minutes. After washing with a FACS buffer twice, 100 µL, each of 200-fold diluted secondary antibody (anti-mouse IgG, FITC-labeled: Jackson immunoresearch) was added to each well and incubated on ice for 20 minutes. After washing with a FACS buffer twice, 20 µL, each of 7-AAD (50 µg/ml) was added to each well and incubated on ice for 20 minutes. After washing with a FACS buffer for three times, the cells were passed through a mesh and finally dissolved in 500 µL, of a FACS buffer. Afterward, FL-1 was detected with FACS Calibur (Japan Becton, Dickinson and Co.), and analyzed with CellQuest.

The results are shown in FIG. 5. α9β1 integrin expression was not found in the human kidney cancer cell line NRC-12 cell but integrins that bind to the RGD sequence such as αvβ3 integrin and α5β1 integrin were expressed.

Example 9

Cell Adhesion and Cell Adhesion Inhibitory Test Using Human Kidney Cancer Cell Line NRC-12 Cell In the same manner as the method in Example 6, cell adhesion activity of the human kidney cancer cell line NRC-12 cell to d.d., a mixture of solid phase d.d. and synthetic peptide (GRGDS) (d.d.+GRGDS), a mixture of d.d. and synthetic peptide (GRGES) (d.d.+GRGES), a synthetic peptide (GRGDS) conjugated with BSA (bovine serum albumin) (GRGDS-BSA), a mixture of a synthetic peptide (GRGDS) conjugated with BSA (bovine serum albumin) and synthetic peptide (GRGDS) (GRGDS-BSA+GRGDS) and a mixture of a synthetic peptide (GRGDS) conjugated with BSA (bovine serum albumin) and a synthetic peptide (GRGES) (GRGDS-BSA+GRGES) were determined In the same manner as the method in Example 6, activity of 8F7 to inhibit cell adhesion of human kidney cancer cell line NRC-12 cell to solid phase d.d. surface was determined.

The results are shown in FIG. 6. The human kidney cancer cell line NRC-12 cell adhered to ADAM-15 d.d. and synthetic peptide GRGDS-BSA in an RGD sequence-dependent manner. The 8F7 antibody inhibited adhesion of the human kidney cancer cell line NRC-12 cell to solid phase d.d. surface in a concentration-dependent manner. As described above, since the human kidney cancer cell line NRC-12 cell does not express α9β1 integrin but expresses integrins that bind to the RGD sequence (αvβ3 integrin, α5β1 integrin), 8F7 seems to suppress cell adhesion due to RGD-dependent interaction between d.d. and the integrin.

Example 10

Expression of Integrin in Human Breast Cancer Cell Line 435S

Expressions of ADAM-15 and integrin in human breast cancer cell line 435S (MDA-MB-435S) was confirmed by flow cytometry. The flow cytometry was performed by following the method described in Example 7.

The results are shown in FIG. 7. Expressions of ADAM-15, αvβ3 integrin, α5β1 integrin and α9β1 integrin were examined in human breast cancer cell line 435S, and all of the molecules were found to be expressed. Their expression levels, however, varied and expression levels of αvβ3 integrin and α5β1 integrin were higher than that of α9β1 integrin.

Example 11

Cell Adhesion and Cell Adhesion Inhibitory Test Using Human Breast Cancer Cell Line 435S Cell Since integrin expressions were confirmed in human breast cancer cell line 435S, whether or not these integrins were functional was examined by a cell adhesion test. Specifically, cell adhesion of 435S to d.d. or d.d.-RAA was determined by the following method. d.d, d.d.-RAA, a protein in which the RGD sequence of recombinant protein of the third fibronectin type III domain present in human tenascin C molecule (hT-Nfn3) was substituted with RAA (hTNfn3(RAA)) and GRGDS-BSA were prepared to be 0 to 5 µg/mL in PBS, and 50 µL, each of them was added to each well of a 96-well plate and incubated at 37° C. for an hour for immobilization. Then, 200 µL, each of 0.5% BSA/PBS was added to each well and incubated at room temperature for an hour for blocking reaction. After washing with PBS, human breast cancer cell line 435S cell was prepared to be $1\times10^5$ cells/ml in 0.25% BSA-containing medium (TIL), and 200 µL, each of which was added to each well and incubated at 37° C. for an hour to allow adhesion to the solid phase protein. Subsequently, washing was performed with PBS that had already been warmed to 37° C. to remove cells that did not adhere. 50 µL each of crystal violet was added to each well and incubated at room temperature for 30 minutes to immobilize and stain the cells. After washing with tap water, 100 µL each of 20% acetic acid in water was added to each well to dissolve the cells, and then absorbance at 590 nm was determined with a plate reader.

The results from the cell adhesion test using human breast cancer cell line 435S cell are shown in FIG. 8A. Human breast cancer cell line 435S adhered to d.d. or d.d.-RAA but its adhesion rate was low.

Previous report proved that integrin was activated with a divalent ion (Mn, Mg, Ca ion or the like). It was also reported that adhesion between ADAM-15 and integrin requires activation of integrin by a divalent ion (Eto, K et al. RGD-independent binding of integrin alpha9beta1 to the ADAM-12 and -15 disintegrin domains mediate cell-cell interaction. J Biol. Chem. 275: 34922-34930, 2000). Hence, integrin was activated with Mn ion in the cell adhesion test using the above-described human breast cancer cell line 435S cell.

The results are shown in FIG. 8B. Addition of Mn ion increased adhesion rate of the human breast cancer cell line 435S cell to d.d. or d.d.-RAA.

Example 12

Cell Adhesion Inhibitory Test Using Human Breast Cancer Cell Line 435S Cell

In the cell adhesion inhibitory test using human breast cancer cell line 435S cell, integrin was activated with use of Mn ion. In the same manner as the cell adhesion test described above, d.d and d.d.-RAA (prepared to be 6.25 μg/ml) were immobilized for blocking reaction. According to the cell adhesion inhibitory activity test for ADAM-15 inhibition, 8F7 was added to protein immobilized on a solid phase. According to the cell adhesion inhibitory activity test for integrin inhibition, an antibody against human α9β1 integrin, i.e., Y9A2 (chemicon), or an antibody against human αvβ3 integrin, i.e., LM-609 (chemicon), was added to $2 \times 10^4$ cells of human breast cancer cell line 435S cells and incubated at 37° C. for 20 minutes. Thereafter, in the same manner as the cell adhesion test, cells were added to each well to determine their cell adhesion.

The results are shown in FIG. 9. As a result of cell adhesion inhibitory test using 8F7 and antibodies against integrins, cell adhesion to d.d. was suppressed with an antibody against αvβ3 integrin but not with an antibody against α9β1 integrin. On the other hand, cell adhesion to d.d.-RAA was suppressed with the antibody against α9β1 integrin. In addition, 8F7 suppressed cell adhesion to both d.d. and d.d.-RAA. Specifically, binding of d.d. including the RGD sequence was found to be mediated by RGD receptor such as αvβ3 integrin but binding mediated by α9β1 integrin was not observed. On the other hand, binding of d.d.-RAA that does not include the RGD sequence was found to be mediated by α9β1 integrin.

As described above, according to the results of confirmation of integrin expression in breast cancer cell line 435S cell by flow cytometry, αvβ3 integrin and α5β1 integrin were strongly expressed as compared to α9β1 integrin. From these facts, αvβ3 integrin and α5β1 integrin appeared to serve predominantly in the binding between ADAM-15 and integrin in the breast cancer cell line 435S cell.

Example 13

Cell Proliferation Test

Human breast cancer cell line 435S cell (MDA-MB-4355: 435S) was prepared to be $2 \times 10^4$ cells/ml in 10% FCS-containing TIL medium, and 100 μL each of which was seeded onto each well of a 96-well plate and cultured at 37° C. overnight. Then, the medium was exchanged with FCS-free TIL medium and similarly cultured overnight. The medium was removed, and 100 μL, each of the antibody (8F7 prepared in Example 5 or anti-human αvβ3 integrin antibody LM-609 (chemicon)) prepared to be 20 μg/ml in 5% FCS-containing TIL medium was added to each well. 10 μL each of cell counting kit-8 (DOUJINDO) was also added to each well. Following incubation at 37° C. for 2 and a half hours, absorbance at 450 nm was determined with a plate reader. This point of time was considered 0 hour, and an experiment was also carried out in a similar procedure with cells cultured for 48 hours in 5% FCS-containing TIL medium including the antibody. The ratio of 450 nm (48 hours)/450 nm (0 hour) was calculated to compare these ratio with those of the non-antibody-added group.

The results are shown in FIG. 10. Addition of 8F7 reduced the cell proliferation rate of the human breast cancer cell line 435S cell by approximately 20%. This suggested that interaction between ADAM-15 and integrin exerts stimulatory influence on the cell proliferation of the breast cancer cell. ADAM-15 disintegrin domain recombinant protein has been reported to inhibit proliferation of breast cancer cells which coincide with the results from this experiment.

(ELISA Method)

According to the examples herein, ELISA method was performed by the following method. First, an antigen was added to a 96-well plate, and immobilized at 4° C. overnight. Then, washing was performed with PBS for 3 times, and 1% BSA/0.05% NaN$_3$/PBS was added at 200 ml/well for blocking reaction. After washing with 0.05% Tween/PBS for 5 times, 100 μL each of the primary antibody diluted in 1% BSA/0.05% Tween/PBS was added to each well and allowed to react at 37° C. for an hour. After washing with 0.05% Tween/PBS for 7 times, the 1000-fold diluted secondary antibody (anti-mouse IgG, HRP-labeled: Jackson immunoresearch) in 1% BSA/0.05% Tween/PBS was added at 50 ml/well and allowed to react at 37° C. for 30 minutes. After washing with 0.05% Tween/PBS for 9 times, o-phenylenediamine solution (Wako) was added at 50 ml/well and allowed to react at room temperature in dark place for 15 minutes. After terminating the reaction with 2N sulfuric acid, absorbance (OD490) was determined with a plate reader.

In antibody titer determination, 50 ng of human ADAM-disintegrin domain-GST protein was immobilized onto each well as an antigen while 1000 to 1000000-fold diluted serum from a mouse immunized with the antigen was used as the primary antibody.

(Statistical Work)

In the cell adhesion inhibitory test herein, OD590 of the non-antibody-added group was used as the standard to calculate the ratio of OD590 obtained for the antibody-added group. In the cell proliferation test, "value after 48 hours/value after 0 hour" was calculated for each group, and the ratio of the antibody-added group was calculated based on the ratio obtained for the non-antibody-added group as the standard. All of these experiments were carried out for 3 times, followed by Student's t-test.

Example 14

Cell Infiltration Inhibitory Test Using Human Breast Cancer Cell Line 435S Cell

Cell infiltration test was performed in order to examine the influence of 8F7 on cell infiltration. The cell infiltration test was carried out by using Matrigel Invasion Chamber (BD). 500 ml each of serum-free TIL medium (Immuno-Biological Laboratories) was added to the well and the insert, and the insert was immersed in the well. Incubation was performed at 37° C. for 2 hours to hydrate the matrigel. Afterward, the medium in the insert was suctioned away, and the insert was immersed in another well containing 750 ml of chemoattractant. As the chemoattractant, culture supernatant of human fibroblastic sarcoma cell line HT-1080 cell was used. 500 ml of 435S cell suspension prepared to be $1 \times 10^5$ cells/ml in serum-free TIL medium was added to the insert and incubated at 37° C. for 22 hours to induce infiltration. For testing the antibody for its cell infiltration inhibitory effect, the 8F7 antibody or the control antibody was added to be 10 mg/ml, incubated at 37° C. for 20 minutes, and the 435S cell suspension was added to the insert prior to the addition of the breast cancer cell to the insert. Following infiltration, the cell suspension in the insert was suctioned away, and the matrigel and the non-infiltrating cells were wiped off with a cotton bud. Then, the insert was immersed in cooled methanol and incubated at −80° C. for 20 minutes to immobilize the infiltrating cell. Following immobilization, the insert was immersed in Giemza solution (Muto Pure Chemicals) for 15 minutes to stain the infiltrating cell. After washing with tap water, filter was removed from the insert, placed on a slide for encapsulation with a mounting agent. The infiltration surface on the bottom face of the filter was observed with an optical microscope, and the number of cells with observable nucleus was counted as infiltrating cells. In this case, the number was counted for six viewing fields and an average value thereof was calculated.

The results are shown in FIG. 11. The number of infiltrating cells without the addition of the antibody was used as the standard, and the rate of the number of the infiltrating cells obtained for the antibody-added group was calculated. These experiments were carried out for 3 times, followed by Student's t-test. Although the number of the infiltrating cells did not change upon addition of the control antibody, the proportion of the infiltrating cells was reduced to approximately 30% upon addition of the 8F7 antibody, confirming that 8F7 has an inhibitory effect on cell infiltration with statistical significance.

Example 15

Amino Acid Sequence Analysis of Antibody

RNA was extracted from hybridoma cells by use of illustra Quickprep Micro mRNA Purification Kit (GE Healthcare Bioscience), from which cDNA was prepared with SuperScript First-strand cDNA for RT-PCR kit (Invitrogen). PCR was performed using heavy primer amplification kit (Amersham Biosciences) and light primer amplification kit (Amersham Biosciences) to elongate the heavy and light chain cDNAs of the antibody. The PCR products of heavy and light chains were integrated into pTAvector (Toyobo Co., Ltd.) and Mighty Cloning Kit <Blunt End> (Takara Bio), respectively, to determine the cDNA sequences and the amino acid sequences. The CDR regions were determined by use of Kabat numbering system.

Primers were prepared based on the cDNA sequences obtained by the above-described method, 5'RACE and 3'RACE was performed for the heavy and light chains of the antibody with GeneRacer Kit (Invitrogen) to perform full-length analysis of the antibody gene. As a result, the amino acid sequences of the heavy and light chains and the CDR regions were as follows (see also FIGS. 12 and 13).

```
(Heavy chain)
[CDRH1]
SYNMH                    (SEQ ID NO: 15)

[CDRH2]
AIYPGDGDTSYNQKFKG        (SEQ ID NO: 16)

[CDRH3]
DRGDYGYGFAY              (SEQ ID NO: 17)

(Light chain)
[CDRL1]
RSSQSLVHSNGNTYLH         (SEQ ID NO: 18)

[CDRL2]
KVSNRFS                  (SEQ ID NO: 19)
```

```
-continued
[CDRL3]
SQNTHVPPWT               (SEQ ID NO: 20)
```

INDUSTRIAL APPLICABILITY

Since an anti-ADAM-15 antibody or the like of the present invention exhibits superior suppressive action against ADAM-15 functions, it can be utilized as a therapeutic or prophylactic drug for a disease caused by cell proliferation, cell migration, cell infiltration, cell-to-cell adhesion or angiogenesis. In particular, the antibody of the present invention can be utilized as a therapeutic or prophylactic drug for cancers (for example, proliferation of cancer cells, metastasis), inflammatory diseases (for example, rheumatoid arthritis, osteoarthritis, hepatitis, bronchial asthma, fibrosis, diabetes, arteriosclerosis, multiple sclerosis, inflammatory bowel disease (ulcerative colitis, Crohn's disease, etc.)), infectious diseases (for example, hepatitis), autoimmune disorders (for example, systemic lupus erythematosus, polymyositis, autoimmune thyroid disease, tubulointerstitial nephritis, myasthenia gravis), skeletal diseases (for example, osteoporosis) and the like. In addition, since the antibody of the present invention is capable of pathologically detecting ADAM-15 expression in a cell or a tissue, it can be employed as a diagnostic drug for the above-mentioned various diseases.

BRIEF DESCRIPTION OF THE DRAWINGS

FIG. 4A shows the results of determination of cell adhesion of CHO-K1 and ha9/CHO to hADAM-15 disintegrin domain. In the figure, the vertical axis represents the absorbance at 590 nm while the horizontal axis represents the concentration of the immobilized polypeptide. FIG. 4B shows the results of determination of inhibitory activity of 8F7 against hα9/CHO cell adhesion to hADAM-15 disintegrin domain. In the figure, the vertical axis represents the absorbance at 590 nm while the horizontal axis represents the concentration of the immobilized polypeptide.

FIG. 6A shows the result from examining cell adhesion between NRC-12 and hADAM-15 disintegrin domain. In the figure, the vertical axis represents the absorbance at 590 nm while the horizontal axis represents the concentration of the immobilized polypeptide. FIG. 6B shows the results of determination of the inhibitory activity of 8F7 against cell adhesion of NRC-12 to hADAM-15 disintegrin domain. In the figure, the vertical axis represents the absorbance at 590 nm while the horizontal axis represents the concentration of the immobilized polypeptide.

FIG. 8A shows the results of determination of cell adhesion to hADAM-15 disintegrin domain. In the figure, the vertical axis represents the absorbance at 590 nm while the horizontal axis represents the concentration of the immobilized polypeptide. FIG. 8B shows the results of determination of cell adhesion to hADAM-15 disintegrin domain in the presence of Mn ion. In the figure, the vertical axis represents the absorbance at 590 nm while the horizontal axis represents the concentration of the immobilized polypeptide.

FIG. 9A shows the results of inhibition of the adhesion of human breast cancer cell line (MDA-MB-435S) to the ADAM-15 disintegrin domain by 8F7. FIG. 9B shows the results of inhibition of adhesion of human breast cancer cell line (MDA-MB-435S) to the ADAM-15 disintegrin domain (RAA substitute) by 8F7. FIG. 9C shows the results of inhibition of adhesion of human breast cancer cell line (MDA-MB-435S) to the ADAM-15 disintegrin domain by Y9A2 or LM609. FIG. 9D shows the results of inhibition of adhesion of human breast cancer cell line (MDA-MB-435S) to the ADAM-15 disintegrin domain (RAA substitute) by Y9A2 or LM609. In all figures, the vertical axes represent the cell adhesion rate considering that of the non-antibody-added case as 100% while the horizontal axes represent the administered antibodies.

FIG. 12 A figure showing the nucleotide sequence and the amino acid sequence of anti-human ADAM-15 antibody (8F7) heavy chain. The amino acid sequence is given in a single letter code. The signal sequence is indicated in italic while the amino acid residue (Q) corresponding to the N terminal of the antibody is double underlined. CDRs analogized by Kabat numbering system are underlined. The amino acid residue (A) at the border of the variable region and the constant region of the antibody is indicated in bold and underlined.

FIG. 13 A figure showing the nucleotide sequence and the amino acid sequence of anti-human ADAM-15 antibody (8F7) light chain. The amino acid sequence is given in a single letter code. The signal sequence is indicated in italic while the amino acid residue (D) corresponding to the N terminal of the antibody is double underlined. CDRs analogized by Kabat numbering system are underlined. The amino acid residue (R) at the border of the variable region and the constant region of the antibody is indicated in bold and underlined.

SEQUENCE LISTING

<160> NUMBER OF SEQ ID NOS: 20

Figure 1:
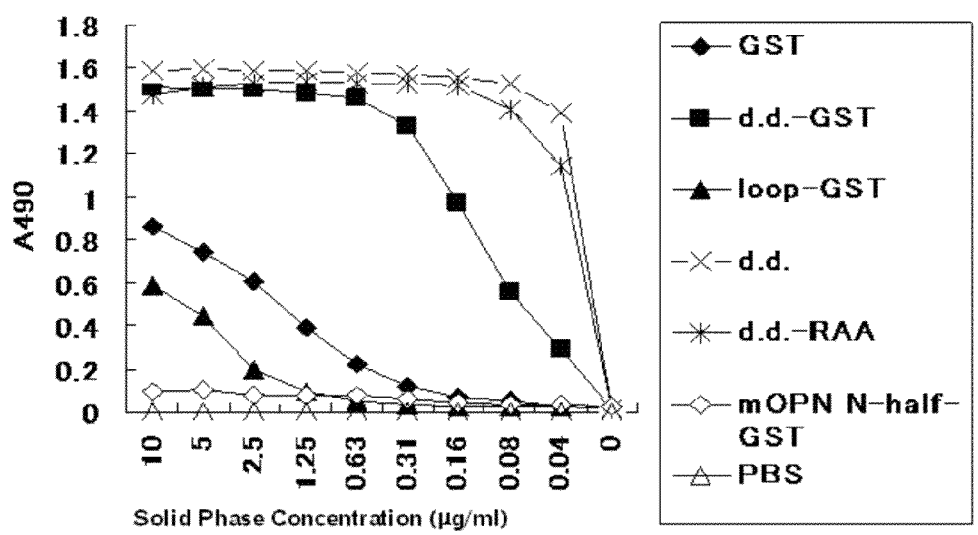
FIG. 1 A figure showing the results of determination of the binding specificity of anti-human ADAM-15 monoclonal antibody 8F7 by ELISA method. In the figure, the vertical axis represents absorbance at 490 nm while the horizontal axis represents concentration of the immobilized polypeptide. Each of GST, human ADAM-15 disintegrin domain-GST protein (d.d.-GST), human ADAM-15 disintegrin domain loop region-GST protein (loop-GST), human ADAM-15 disintegrin domain protein (d.d.), human ADAM-15 disintegrin domain protein (RAA substitute) (d.d.-RAA) and mouse osteopontin N-half-GST protein (mOPN N-half-GST) was immobilized on a solid phase in serial dilutions from 10 μg/ml, while 8F7 prepared to be 0.1 μg/ml was used as the primary antibody. Absorbance of PBS alone was used as the baseline.
Figure 2:
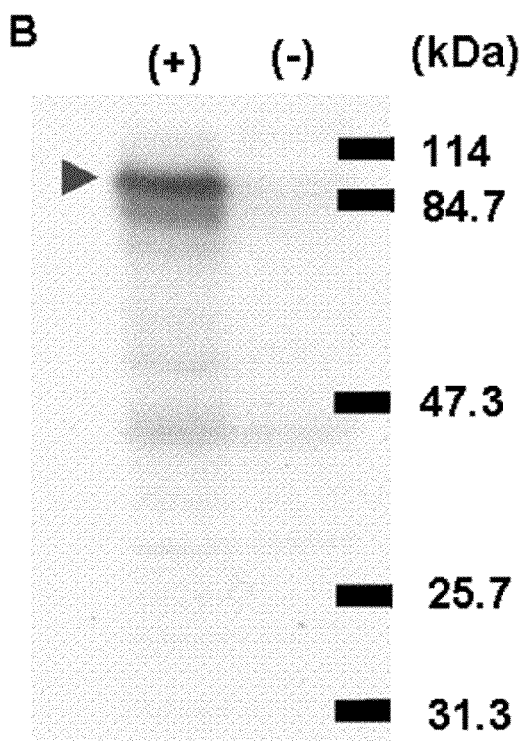
FIG. 2 A figure showing the results of determination of the binding specificity of human ADAM-15 monoclonal antibody 8F7 by Western blot. In the figure, (+) represents the sample of ADAM-15-transfected COS-7 cell solution while (−) represents the sample of untransfected COS-7 cell solution. In addition, the arrow points the band of interest.
Figure 3:
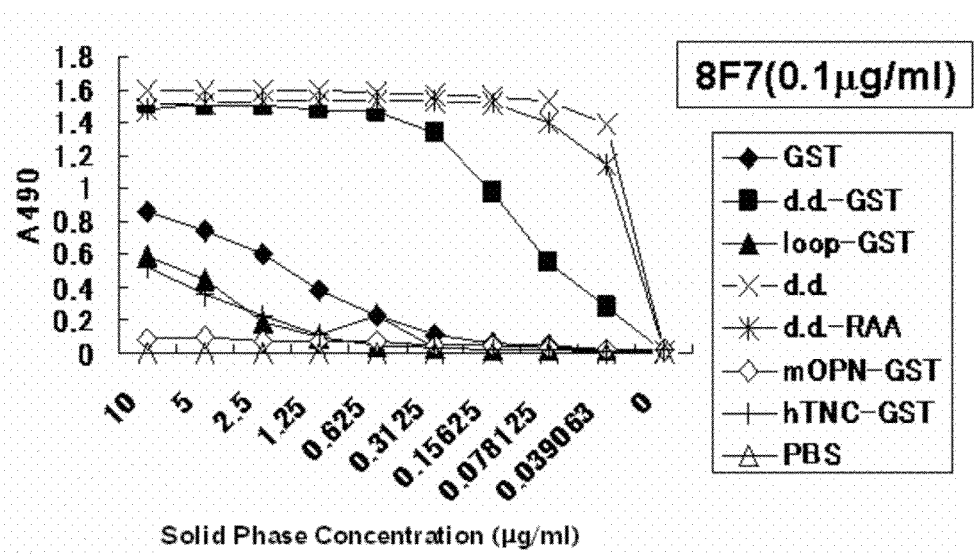
FIG. 3 A figure showing the results of determination of the binding activities of 8F7 and 23G9 to the ADAM-15 disintegrin domain by ELISA method. In the figure, the vertical axis represents the absorbance at 490 nm while the horizontal axis represents the concentration of the immobilized polypeptide. Furthermore, hTNC-GST stands for human/tenascin C-GST protein.
Figure 3:
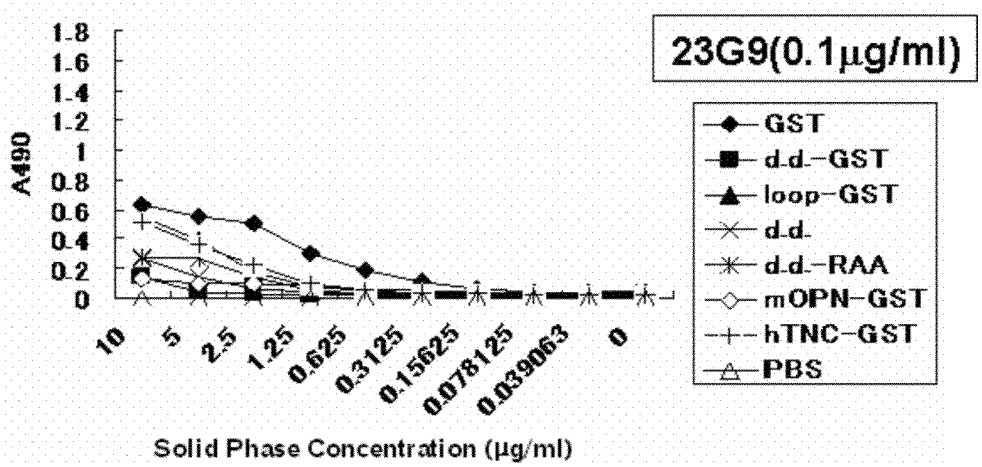
Figure 4:
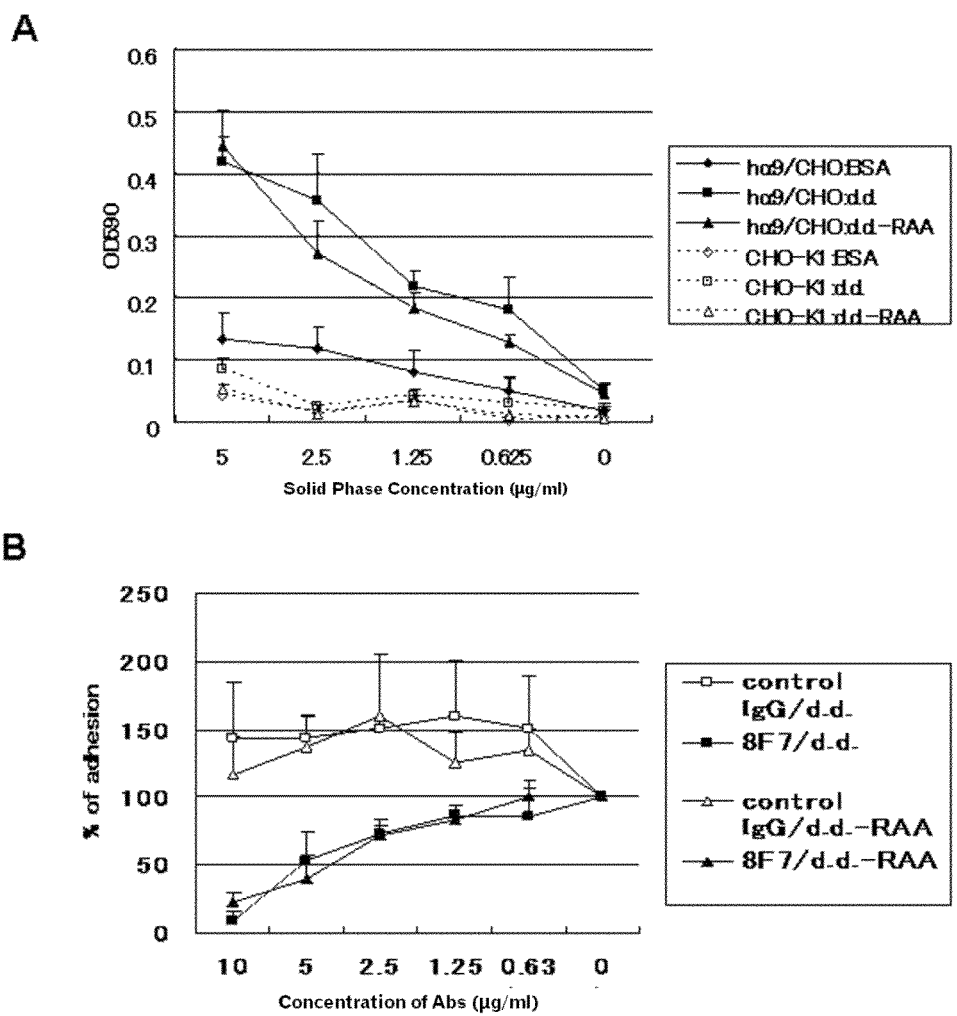
FIG. 4 A figure showing the results of determination of RGD sequence-independent cell adhesion inhibitory activity of 8F7.
Figure 5:
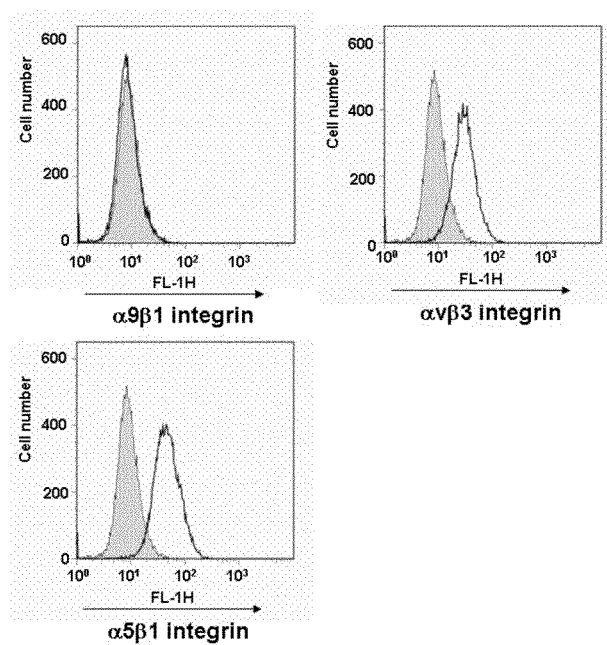
FIG. 5 A figure showing the results of determination of integrin expression in human kidney cancer cell line NRC-12 by flow cytometry. α9β1 integrin, αvβ3 integrin and α5β1 integrin were detected with Y9A2, LM609 and JBS5, respectively.
Figure 6:
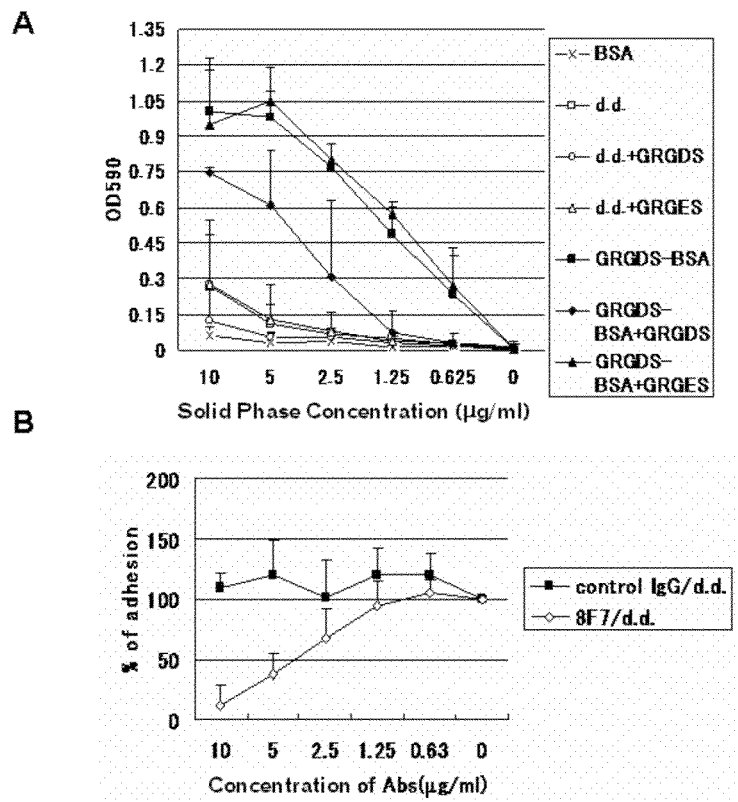
FIG. 6 A figure showing the results of determination of inhibitory activity of 8F7 against RGD sequence-dependent cell adhesion.
Figure 7:
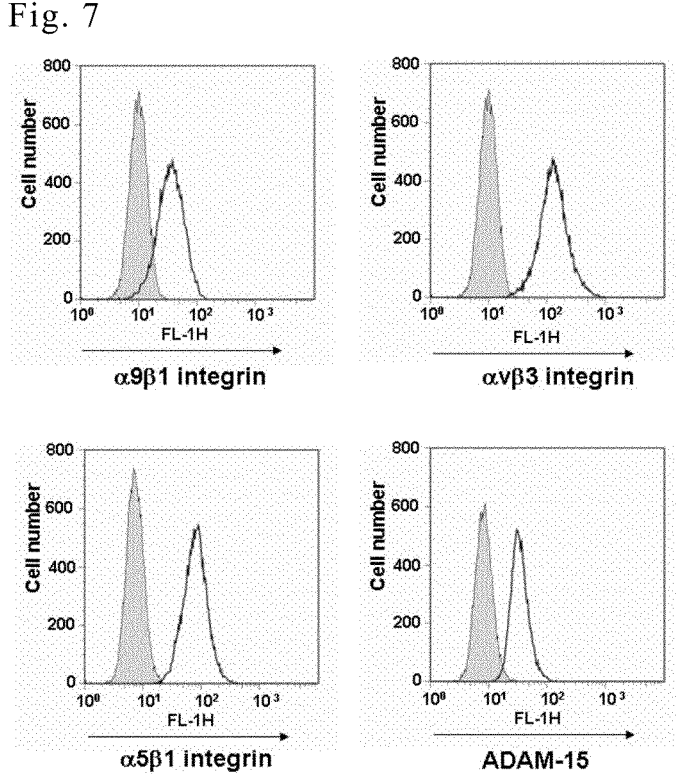
FIG. 7 A figure showing the results of determination of integrin expression in human breast cancer cell line (MDA-MB-4355) by flow cytometry. α9β1 integrin, αvβ3 integrin and α5β1 integrin were detected with Y9A2, LM609 and JBS5, respectively.
Figure 8:
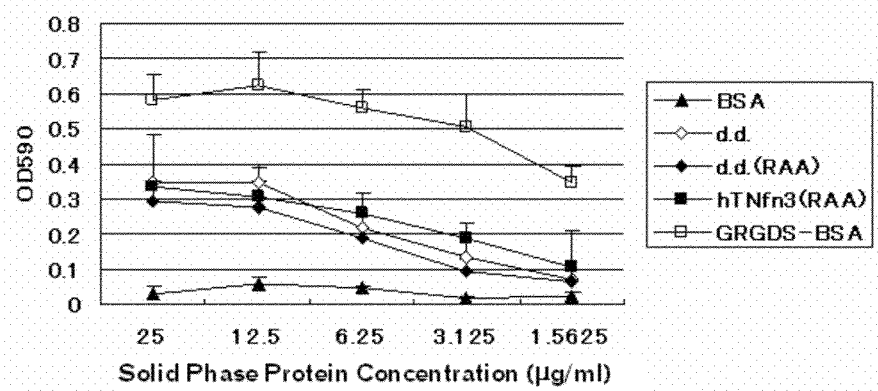
FIG. 8 A figure showing the result from the cell adhesion test using human breast cancer cell line (MDA-MB-435S).
Figure 8:
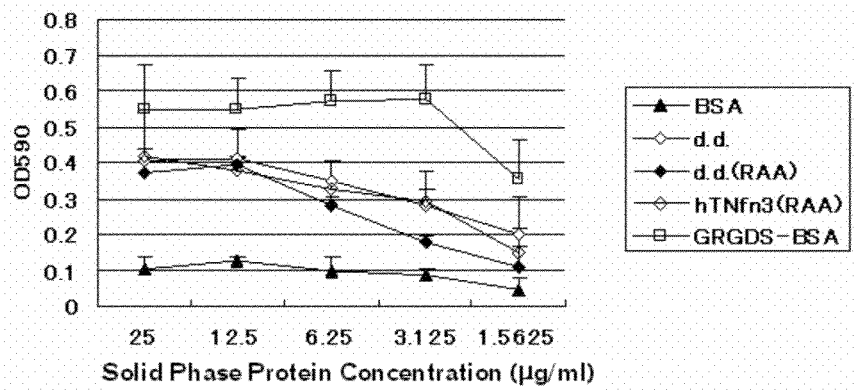
Figure 9:
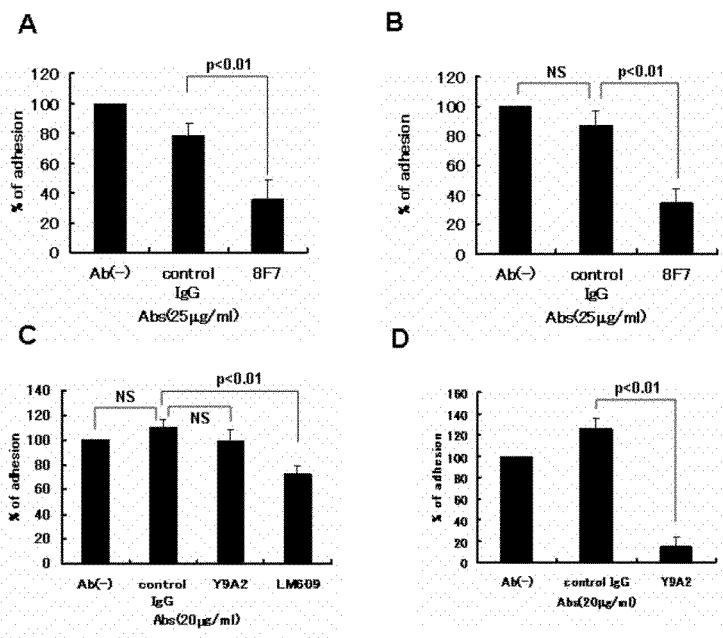
FIG. 9 A figure showing the results from the cell adhesion inhibitory test using human breast cancer cell line (MDA-MB-435S).
Figure 10:
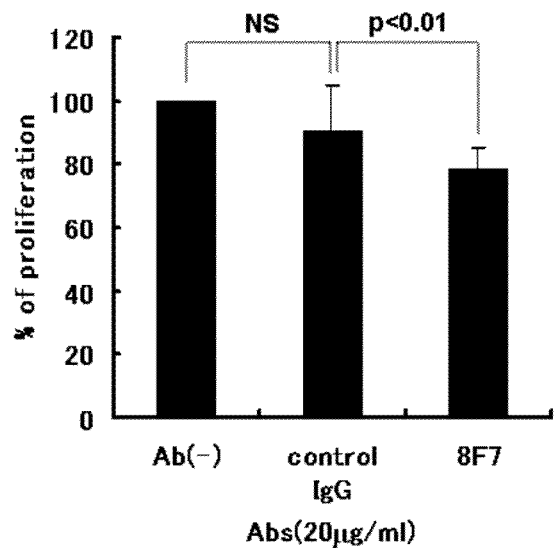
FIG. 10 A figure showing the results of determination of the ADAM-15 functions upon cell proliferation of human breast cancer cell line (MDA-MB-435S) and the inhibitory activity by 8F7 against these functions. Each antibody was added at 20 μg/mL. In the figure, the vertical axis represents the cell proliferation rate after 48 hours.
Figure 11:
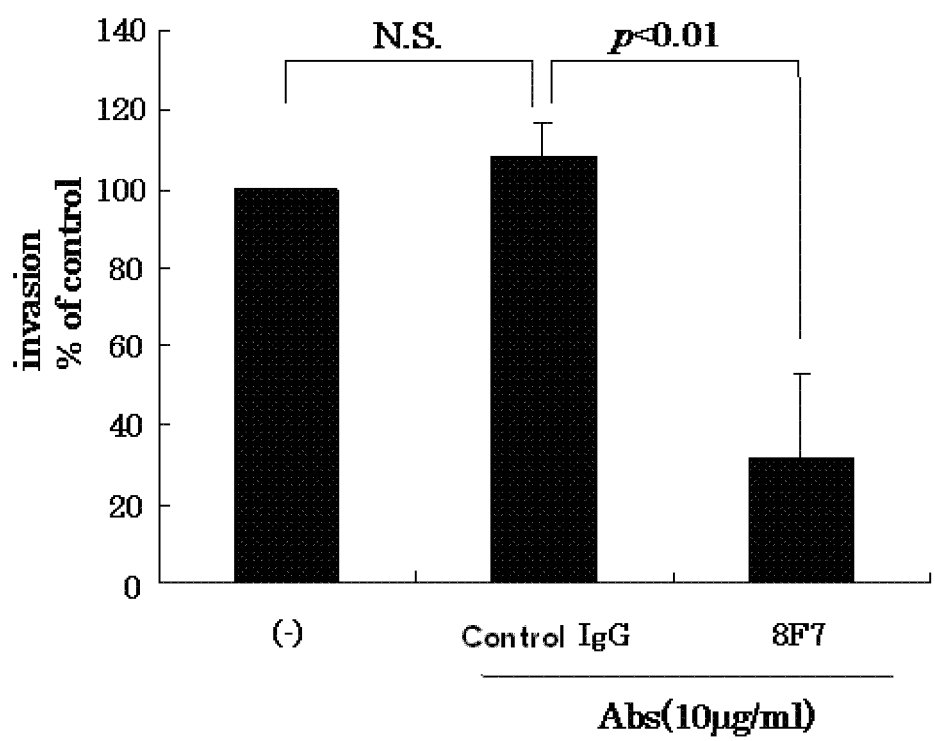
FIG. 11 A figure showing the results from the cell infiltration inhibitory test using human breast cancer cell line 435S cells.

<210> SEQ ID NO 1
<211> LENGTH: 32
<212> TYPE: DNA
<213> ORGANISM: Artificial
<220> FEATURE:
<223> OTHER INFORMATION: Sense Primer

<400> SEQUENCE: 1
ttttaagctt gccaccatgg gcggcccggc tg                                  32

<210> SEQ ID NO 2
<211> LENGTH: 33
<212> TYPE: DNA
<213> ORGANISM: Artificial
<220> FEATURE:
<223> OTHER INFORMATION: Antisense Primer

<400> SEQUENCE: 2
aaactgcagt ccggagcact ggatttatct tct                                 33

<210> SEQ ID NO 3
<211> LENGTH: 24
<212> TYPE: DNA
<213> ORGANISM: Artificial
<220> FEATURE:
<223> OTHER INFORMATION: Sense Primer

<400> SEQUENCE: 3
aaatccggat gtttggtcca tatc                                              24

<210> SEQ ID NO 4
<211> LENGTH: 33
<212> TYPE: DNA
<213> ORGANISM: Artificial
<220> FEATURE:
<223> OTHER INFORMATION: Antisense Primer

<400> SEQUENCE: 4
aaatctagat cactggtttt tctggaccca gtc                                    33

<210> SEQ ID NO 5
<211> LENGTH: 18
<212> TYPE: DNA
<213> ORGANISM: Artificial
<220> FEATURE:
<223> OTHER INFORMATION: Sense Primer

<400> SEQUENCE: 5
cctatggctg ctttctgc                                                     18

<210> SEQ ID NO 6
<211> LENGTH: 18
<212> TYPE: DNA
<213> ORGANISM: Artificial
<220> FEATURE:
<223> OTHER INFORMATION: Antisense Primer

<400> SEQUENCE: 6
catgcacaca gcttgccc                                                     18

<210> SEQ ID NO 7
<211> LENGTH: 23
<212> TYPE: DNA
<213> ORGANISM: Artificial
<220> FEATURE:
<223> OTHER INFORMATION: Sense Primer

<400> SEQUENCE: 7
aaggatccgc tgctttctgc gga                                               23

<210> SEQ ID NO 8
<211> LENGTH: 26
<212> TYPE: DNA
<213> ORGANISM: Artificial
<220> FEATURE:
<223> OTHER INFORMATION: Antisense Primer

<400> SEQUENCE: 8
attctcgaga tcccctaggc tgacat                                            26

<210> SEQ ID NO 9
<211> LENGTH: 34
<212> TYPE: DNA
<213> ORGANISM: Artificial
<220> FEATURE:
<223> OTHER INFORMATION: Sense Primer -continued

<400> SEQUENCE: 9
cagtgtccta ccagagctgc ttgtgacttg cctg                34

<210> SEQ ID NO 10
<211> LENGTH: 37
<212> TYPE: DNA
<213> ORGANISM: Artificial
<220> FEATURE:
<223> OTHER INFORMATION: Antisense Primer

<400> SEQUENCE: 10
caggcaagtc acaagcagct ctggtaggac gacactg            37

<210> SEQ ID NO 11
<211> LENGTH: 1134
<212> TYPE: DNA
<213> ORGANISM: Mus musculus
<220> FEATURE:
<221> NAME/KEY: CDS
<222> LOCATION: (1)..(1134)

<400> SEQUENCE: 11

```
atg gga tgg agt tgt atc atc ctc ttc ttg gta gca aca gct aca ggt       48
Met Gly Trp Ser Cys Ile Ile Leu Phe Leu Val Ala Thr Ala Thr Gly
1               5                   10                  15 gtc cac tcc cag gtg caa ctg cag cag cct ggg gct gag ctg gtg aag       96
Val His Ser Gln Val Gln Leu Gln Gln Pro Gly Ala Glu Leu Val Lys
            20                  25                  30 cct ggg gcc tca gtg aag gtg tcc tgc aag gct tct gcc tac aca ttt      144
Pro Gly Ala Ser Val Lys Val Ser Cys Lys Ala Ser Ala Tyr Thr Phe
        35                  40                  45 acc agt tac aat atg cac tgg gta aag cag aca cct gga cag ggc ctg      192
Thr Ser Tyr Asn Met His Trp Val Lys Gln Thr Pro Gly Gln Gly Leu
    50                  55                  60 gaa tgg att gga gct att tat cca gga gat ggt gat act tcc tac aat      240
Glu Trp Ile Gly Ala Ile Tyr Pro Gly Asp Gly Asp Thr Ser Tyr Asn
65                  70                  75                  80 cag aaa ttc aaa ggc aag gcc aca ttg act gca gac aaa tcc tcc agc      288
Gln Lys Phe Lys Gly Lys Ala Thr Leu Thr Ala Asp Lys Ser Ser Ser
                85                  90                  95 aca gcc tac att cat ctc agc agc ctg aca tct gag gac tct gcg gtc      336
Thr Ala Tyr Ile His Leu Ser Ser Leu Thr Ser Glu Asp Ser Ala Val
            100                 105                 110 tat tac tgt gca aga gac agg ggg gac tac ggc tac ggg ttt gct tac      384
Tyr Tyr Cys Ala Arg Asp Arg Gly Asp Tyr Gly Tyr Gly Phe Ala Tyr
        115                 120                 125 tgg ggc caa ggg act ctg gtc act gtc tct gca gcc aaa acg aca ccc      432
Trp Gly Gln Gly Thr Leu Val Thr Val Ser Ala Ala Lys Thr Thr Pro
    130                 135                 140 cca tct gtc tat cca ctg gcc cct gga tct gct gcc caa act aac tcc      480
Pro Ser Val Tyr Pro Leu Ala Pro Gly Ser Ala Ala Gln Thr Asn Ser
145                 150                 155                 160 atg gtg acc ctg gga tgc ctg gtc aag ggc tat ttc cct gag cca gtg      528
Met Val Thr Leu Gly Cys Leu Val Lys Gly Tyr Phe Pro Glu Pro Val
                165                 170                 175 aca gtg acc tgg aac tct gga tcc ctg tcc agc ggt gtg cac acc ttc      576
Thr Val Thr Trp Asn Ser Gly Ser Leu Ser Ser Gly Val His Thr Phe
            180                 185                 190 cca gct gtc ctg cag tct gac ctc tac act ctg agc agc tca gtg act      624
Pro Ala Val Leu Gln Ser Asp Leu Tyr Thr Leu Ser Ser Ser Val Thr
        195                 200                 205 gtc ccc tcc agc acc tgg ccc agc gag acc gtc acc tgc aac gtt gcc      672
```

```
                                                             -continued

Val Pro Ser Ser Thr Trp Pro Ser Glu Thr Val Thr Cys Asn Val Ala
    210                 215                 220 cac ccg gcc agc agc acc aag gtg gac aag aaa att gtg ccc agg gat      720
His Pro Ala Ser Ser Thr Lys Val Asp Lys Lys Ile Val Pro Arg Asp
225                 230                 235                 240 tgt ggt tgt aag cct tgc ata tgt aca gtc cca gaa gta tca tct gtc      768
Cys Gly Cys Lys Pro Cys Ile Cys Thr Val Pro Glu Val Ser Ser Val
                245                 250                 255 ttc atc ttc ccc cca aag ccc aag gat gtg ctc acc att act ctg act      816
Phe Ile Phe Pro Pro Lys Pro Lys Asp Val Leu Thr Ile Thr Leu Thr
                260                 265                 270 cct aag gtc acg tgt gtt gtg gta gac atc agc aag gat gat ccc gag      864
Pro Lys Val Thr Cys Val Val Val Asp Ile Ser Lys Asp Asp Pro Glu
            275                 280                 285 gtc cag ttc agc tgg ttt gta gat gat gtg gag gtg cac aca gct cag      912
Val Gln Phe Ser Trp Phe Val Asp Asp Val Glu Val His Thr Ala Gln
        290                 295                 300 acg caa ccc cgg gag gag cag ttc aac agc act ttc cgc tca gtc agt      960
Thr Gln Pro Arg Glu Glu Gln Phe Asn Ser Thr Phe Arg Ser Val Ser
305                 310                 315                 320 gaa ctt ccc atc atg cac cag gac tgg ctc aat ggc aag gag ttc aaa     1008
Glu Leu Pro Ile Met His Gln Asp Trp Leu Asn Gly Lys Glu Phe Lys
                325                 330                 335 tgc agg gtc aac agt gca gct ttc cct gcc ccc atc gag aaa acc atc     1056
Cys Arg Val Asn Ser Ala Ala Phe Pro Ala Pro Ile Glu Lys Thr Ile
                340                 345                 350 tcc aaa acc aaa ggc aga ccg aag gct cca cag gtg tac acc att cca     1104
Ser Lys Thr Lys Gly Arg Pro Lys Ala Pro Gln Val Tyr Thr Ile Pro
            355                 360                 365 cct ccc aag gag cag atg gcc aaa gga taa                              1134
Pro Pro Lys Glu Gln Met Ala Lys Gly
        370                 375

<210> SEQ ID NO 12
<211> LENGTH: 377
<212> TYPE: PRT
<213> ORGANISM: Mus musculus

<400> SEQUENCE: 12

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Lys
                20                  25                  30

Pro Gly Ala Ser Val Lys Val Ser Cys Lys Ala Ser Ala Tyr Thr Phe
            35                  40                  45

Thr Ser Tyr Asn Met His Trp Val Lys Gln Thr Pro Gly Gln Gly Leu
        50                  55                  60

Glu Trp Ile Gly Ala Ile Tyr Pro Gly Asp Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Ile His Leu Ser Ser Leu Thr Ser Glu Asp Ser Ala Val
            100                 105                 110

Tyr Tyr Cys Ala Arg Asp Arg Gly Asp Tyr Gly Tyr Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr Pro Leu Ala Pro Gly Ser Ala Ala Gln Thr Asn Ser
145                 150                 155                 160
```

```
Met Val Thr Leu Gly Cys Leu Val Lys Gly Tyr Phe Pro Glu Pro Val
            165                 170                 175

Thr Val Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
            195                 200                 205

Val Pro Ser Ser Thr Trp Pro Ser Glu Thr Val Thr Cys Asn Val Ala
210                 215                 220

His Pro Ala Ser Ser Thr Lys Val Asp Lys Lys Ile Val Pro Arg Asp
225                 230                 235                 240

Cys Gly Cys Lys Pro Cys Ile Cys Thr Val Pro Glu Val Ser Ser Val
            245                 250                 255

Phe Ile Phe Pro Pro Lys Pro Lys Asp Val Leu Thr Ile Thr Leu Thr
            260                 265                 270

Pro Lys Val Thr Cys Val Val Val Asp Ile Ser Lys Asp Asp Pro Glu
            275                 280                 285

Val Gln Phe Ser Trp Phe Val Asp Asp Val Glu Val His Thr Ala Gln
            290                 295                 300

Thr Gln Pro Arg Glu Glu Gln Phe Asn Ser Thr Phe Arg Ser Val Ser
305                 310                 315                 320

Glu Leu Pro Ile Met His Gln Asp Trp Leu Asn Gly Lys Glu Phe Lys
            325                 330                 335

Cys Arg Val Asn Ser Ala Ala Phe Pro Ala Pro Ile Glu Lys Thr Ile
            340                 345                 350

Ser Lys Thr Lys Gly Arg Pro Lys Ala Pro Gln Val Tyr Thr Ile Pro
            355                 360                 365

Pro Pro Lys Glu Gln Met Ala Lys Gly
            370                 375

<210> SEQ ID NO 13
<211> LENGTH: 720
<212> TYPE: DNA
<213> ORGANISM: Mus musculus
<220> FEATURE:
<221> NAME/KEY: CDS
<222> LOCATION: (1)..(720)

<400> SEQUENCE: 13 atg aag ttg cct gtt agg ctg ttg gtg ctg atg ttc tgg att cct gct      48
Met Lys Leu Pro Val Arg Leu Leu Val Leu Met Phe Trp Ile Pro Ala
1               5                   10                  15 tcc agc agt gat gtt gtg atg acc caa act cca ctc tcc ctg cct gtc     96
Ser Ser Ser Asp Val Val Met Thr Gln Thr Pro Leu Ser Leu Pro Val
                20                  25                  30 agt ctt gga gat caa gcc tcc atc tct tgc aga tct agt cag agc ctt    144
Ser Leu Gly Asp Gln Ala Ser Ile Ser Cys Arg Ser Ser Gln Ser Leu
            35                  40                  45 gta cac agt aat gga aac acc tat tta cat tgg tac ctg cac aag cca    192
Val His Ser Asn Gly Asn Thr Tyr Leu His Trp Tyr Leu His Lys Pro
        50                  55                  60 ggc cag tct cca aag ctc ctg atc tac aaa gtt tcc aac cga ttt tct    240
Gly Gln Ser Pro Lys Leu Leu Ile Tyr Lys Val Ser Asn Arg Phe Ser
65                  70                  75                  80 ggg gtc cca gac agg ttc agt ggc agt gga tca ggg aca gat ttc aca    288
Gly Val Pro Asp Arg Phe Ser Gly Ser Gly Ser Gly Thr Asp Phe Thr
                85                  90                  95 ctc aag atc agc aga gtg gag gct gag gat ctg gga gtt tat ttc tgc    336
Leu Lys Ile Ser Arg Val Glu Ala Glu Asp Leu Gly Val Tyr Phe Cys
```

```
                                100                           105                           110
         tct caa aat aca cat gtt cct ccg tgg acg ttc ggt gga ggc acc aag       384
         Ser Gln Asn Thr His Val Pro Pro Trp Thr Phe Gly Gly Gly Thr Lys
                 115                           120                           125 ctg gaa atc aaa cgg gct gat gct gca cca act gta tcc atc ttc cca       432
         Leu Glu Ile Lys Arg Ala Asp Ala Ala Pro Thr Val Ser Ile Phe Pro
         130                           135                           140 cca tcc agt gag cag tta aca tct gga ggt gcc tca gtc gtg tgc ttc       480
         Pro Ser Ser Glu Gln Leu Thr Ser Gly Gly Ala Ser Val Val Cys Phe
         145                           150                           155                       160 ttg aac aac ttc tac ccc aaa gac atc aat gtc aag tgg aag att gat       528
         Leu Asn Asn Phe Tyr Pro Lys Asp Ile Asn Val Lys Trp Lys Ile Asp
                         165                           170                           175 ggc agt gaa cga caa aat ggc gtc ctg aac agt tgg act gat cag gac       576
         Gly Ser Glu Arg Gln Asn Gly Val Leu Asn Ser Trp Thr Asp Gln Asp
                         180                           185                           190 agc aaa gac agc acc tac agc atg agc agc acc ctc acg ttg acc aag       624
         Ser Lys Asp Ser Thr Tyr Ser Met Ser Ser Thr Leu Thr Leu Thr Lys
                         195                           200                           205 gac gag tat gaa cga cat aac agc tat acc tgt gag gcc act cac aag       672
         Asp Glu Tyr Glu Arg His Asn Ser Tyr Thr Cys Glu Ala Thr His Lys
         210                           215                           220 aca tca act tca ccc att gtc aag agc ttc aac agg aat gag tgt tag       720
         Thr Ser Thr Ser Pro Ile Val Lys Ser Phe Asn Arg Asn Glu Cys
         225                           230                           235

<210> SEQ ID NO 14
         <211> LENGTH: 239
         <212> TYPE: PRT
         <213> ORGANISM: Mus musculus

<400> SEQUENCE: 14

Met Lys Leu Pro Val Arg Leu Leu Val Leu Met Phe Trp Ile Pro Ala
         1               5                   10                  15

Ser Ser Ser Asp Val Val Met Thr Gln Thr Pro Leu Ser Leu Pro Val
                         20                  25                  30

Ser Leu Gly Asp Gln Ala Ser Ile Ser Cys Arg Ser Ser Gln Ser Leu
                     35                  40                  45

Val His Ser Asn Gly Asn Thr Tyr Leu His Trp Tyr Leu His Lys Pro
         50                  55                  60

Gly Gln Ser Pro Lys Leu Leu Ile Tyr Lys Val Ser Asn Arg Phe Ser
         65                  70                  75                  80

Gly Val Pro Asp Arg Phe Ser Gly Ser Gly Ser Gly Thr Asp Phe Thr
                         85                  90                  95

Leu Lys Ile Ser Arg Val Glu Ala Glu Asp Leu Gly Val Tyr Phe Cys
                     100                 105                 110

Ser Gln Asn Thr His Val Pro Pro Trp Thr Phe Gly Gly Gly Thr Lys
                     115                 120                 125

Leu Glu Ile Lys Arg Ala Asp Ala Ala Pro Thr Val Ser Ile Phe Pro
         130                 135                 140

Pro Ser Ser Glu Gln Leu Thr Ser Gly Gly Ala Ser Val Val Cys Phe
         145                 150                 155                 160

Leu Asn Asn Phe Tyr Pro Lys Asp Ile Asn Val Lys Trp Lys Ile Asp
                         165                 170                 175

Gly Ser Glu Arg Gln Asn Gly Val Leu Asn Ser Trp Thr Asp Gln Asp
                     180                 185                 190

Ser Lys Asp Ser Thr Tyr Ser Met Ser Ser Thr Leu Thr Leu Thr Lys
                     195                 200                 205
```

```
Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235
```

<210> SEQ ID NO 15
<211> LENGTH: 5
<212> TYPE: PRT
<213> ORGANISM: Mus musculus

<400> SEQUENCE: 15

```
Ser Tyr Asn Met His
1               5
```

<210> SEQ ID NO 16
<211> LENGTH: 17
<212> TYPE: PRT
<213> ORGANISM: Mus musculus

<400> SEQUENCE: 16

```
Ala Ile Tyr Pro Gly Asp Gly Asp Thr Ser Tyr Asn Gln Lys Phe Lys
1               5                   10                  15

Gly
```

<210> SEQ ID NO 17
<211> LENGTH: 11
<212> TYPE: PRT
<213> ORGANISM: Mus musculus

<400> SEQUENCE: 17

```
Asp Arg Gly Asp Tyr Gly Tyr Gly Phe Ala Tyr
1               5                   10
```

<210> SEQ ID NO 18
<211> LENGTH: 16
<212> TYPE: PRT
<213> ORGANISM: Mus musculus

<400> SEQUENCE: 18

```
Arg Ser Ser Gln Ser Leu Val His Ser Asn Gly Asn Thr Tyr Leu His
1               5                   10                  15
```

<210> SEQ ID NO 19
<211> LENGTH: 7
<212> TYPE: PRT
<213> ORGANISM: Mus musculus

<400> SEQUENCE: 19

```
Lys Val Ser Asn Arg Phe Ser
1               5
```

<210> SEQ ID NO 20
<211> LENGTH: 10
<212> TYPE: PRT
<213> ORGANISM: Mus musculus

<400> SEQUENCE: 20

```
Ser Gln Asn Thr His Val Pro Pro Trp Thr
1               5                   10
```

The invention claimed is:

1. An isolated antibody or a fragment thereof that recognizes ADAM-15 disintegrin domain, but that does not recognize RGD sequence in the ADAM-15 disintegrin domain or loop region in the ADAM-15 disintegrin domain, wherein said antibody or fragment thereof comprises:
   a CDR1, CDR2 and CDR3 of the heavy chain variable region comprising the amino acid sequences of SEQ ID NO:15, SEQ ID NO: 16 and SEQ ID NO: 17, respectively, and
   a CDR1, CDR2 and CDR3 of the light chain variable region comprising the amino acid sequences of SEQ ID NO: 18, SEQ ID NO: 19 and SEQ ID NO: 20, respectively.

2. The antibody or the fragment thereof according to claim 1, which inhibits ADAM-15 and integrin $\alpha v\beta 3$-dependent cell adhesion.

3. The antibody or the fragment thereof according to claim 1, which inhibits ADAM-15 and integrin $\alpha 9\beta 1$-dependent cell adhesion.

4. The antibody or the fragment thereof according to claim 1, characterized by suppressing proliferation of a cancer cell.

5. The antibody or the fragment thereof according to claim 1, wherein the antibody is a monoclonal antibody.

6. The antibody or the fragment thereof according to claim 1, wherein the antibody comprises a heavy chain having the amino acid sequence represented by SEQ ID NO:12 and/or a light chain having the amino acid sequence represented by SEQ ID NO:14.

7. The antibody or the fragment thereof according to claim 5, wherein the antibody is a monoclonal antibody produced by a hybridoma cell deposited under Accession No. FERM BP-10950.

8. The antibody or the fragment thereof according to claim 1, wherein the antibody is a chimeric antibody, or a humanized antibody.

9. The antibody or the fragment thereof according to claim 1, wherein the antibody fragment is F(ab')$_2$, Fab', Fab, single-chain Fv (scFv), disulfide-linked Fv (dsFv), a polymer thereof or dimeric V region (diabody).

10. An isolated DNA coding for the antibody or the fragment thereof according to claim 1.

11. A recombinant vector comprising the DNA according to claim 10.

12. A transformed cell obtained by introducing the recombinant vector according to claim 11 into a host cell.

13. The cell according to claim 12 which is a hybridoma cell line.

14. The cell according to claim 13 which is a hybridoma cell line defined by Accession No. FERM BP-10950.

15. A method for producing the antibody or the fragment thereof the method comprising the steps of: culturing the cell according to claim 12 under conditions to produce the antibody or the fragment thereof in the culture; and extracting the antibody or the fragment thereof from the culture.

16. A pharmaceutical composition comprising the antibody or the fragment thereof according to claim 1 as an active element.

17. The pharmaceutical composition according to claim 16, which is a therapeutic drug or a prophylactic drug for a disease caused by cell proliferation, cell migration, cell infiltration, cell-to-cell adhesion or angiogenesis.

18. The pharmaceutical composition according to claim 16, which is an antitumor agent or a metastasis-suppressing agent for cancer.

19. A diagnostic drug comprising the antibody or the fragment thereof according to claim 1.

20. The diagnostic drug according to claim 19, which is a diagnostic drug for a disease caused by cell proliferation, cell migration, cell infiltration, cell-to-cell adhesion or angiogenesis.

21. An isolated polynucleotide encoding an antibody comprising the amino acid sequences represented by SEQ ID NOs:15, 16, 17, 18 19 and 20.

22. A recombinant vector comprising the nucleotide according to claim 21.

* * * * *